United States Patent
Mabrouk et al.

(10) Patent No.: US 10,064,814 B2
(45) Date of Patent: Sep. 4, 2018

(54) USE OF SPIDER VENOMS FOR SKIN WHITENING/DEPIGMENTING AND COMPOSITION COMPRISING SPIDER VENOMS MOLECULES OR SYNTHETIC ANALOGS

(71) Applicants: LABORATOIRE IN'OYA, Gardanne (FR); LATOXAN, Valence (FR); UNIVERSITE AIX-MARSEILLE, Marseilles (FR)

(72) Inventors: Kamel Mabrouk, Les Pennes Mirabeau (FR); Jose Luis, chemin du Gregau (FR); Harold De Pomyers, Marsaz (FR); Denis Bertin, Marseilles (FR); Abd Haq Bengeloune, Aix-en-Provence (FR); Marion Verdoni, Marseilles (FR); Didier Gigmes, Allauch (FR); Hermine Roudaut, Marseilles (FR)

(73) Assignees: LABORATOIRE IN'OYA, Gardanne (FR); LATOXAN, Valence (FR); UNIVERSITE AIX-MARSEILLE, Marseilles (FR)

( * ) Notice: Subject to any disclaimer, the term of this patent is extended or adjusted under 35 U.S.C. 154(b) by 0 days.

(21) Appl. No.: 14/425,732

(22) PCT Filed: Sep. 5, 2013

(86) PCT No.: PCT/EP2013/002666
§ 371 (c)(1),
(2) Date: Mar. 4, 2015

(87) PCT Pub. No.: WO2014/037111
PCT Pub. Date: Mar. 13, 2014

(65) Prior Publication Data
US 2015/0231061 A1    Aug. 20, 2015

(30) Foreign Application Priority Data
Sep. 5, 2012 (EP) .................................. 12006270

(51) Int. Cl.
*A61K 36/00* (2006.01)
*A61K 8/98* (2006.01)
*A61K 8/43* (2006.01)
*A61Q 19/02* (2006.01)

(52) U.S. Cl.
CPC ............... *A61K 8/987* (2013.01); *A61K 8/43* (2013.01); *A61Q 19/02* (2013.01); *A61K 2800/40* (2013.01)

(58) Field of Classification Search
CPC .................................................... A61K 36/00
USPC ........................................................ 424/725
See application file for complete search history.

(56) References Cited

FOREIGN PATENT DOCUMENTS

WO      WO 94/18959      *  9/1994

\* cited by examiner

*Primary Examiner* — Michael V Meller
(74) *Attorney, Agent, or Firm* — Young & Thompson

(57) ABSTRACT

The use of spider venom, molecules or synthetic analogs thereof for skin whitening. Also, compositions that include spider venom, molecules or synthetic analogs thereof for skin whitening/depigmenting, and a non-therapeutic method for whitening human skin that includes topically applying an effective amount on human skin of the composition.

1 Claim, 17 Drawing Sheets

US 10,064,814 B2

USE OF SPIDER VENOMS FOR SKIN WHITENING/DEPIGMENTING AND COMPOSITION COMPRISING SPIDER VENOMS MOLECULES OR SYNTHETIC ANALOGS

This international patent application claims the priority of European patent EP 12006270.8 filed on Sep. 5, 2012, which herein incorporated by reference.

FIELD OF THE INVENTION

The present invention relates to the use of spider venoms for skin whitening/depigmenting and to compositions comprising spider venoms molecules or synthetic analogs.

BACKGROUND OF THE INVENTION

Melanogenesis is the scientific term to refer to skin pigmentation. Although melanogenesis is necessary as a mechanism of defense against UV radiation, a disruption of this process may cause an abnormal accumulation of melanin called hyperpigmentation, including melisma and senile lentigines.

The evolution of the melanogenesis pathway takes place in the epidermis, in particular in dendritic cells, which interact with keratinocytes: melanocytes. These latter contain specific organelles called melanosomes: site of the synthesis of different pigments (melanins), responsible for our specific skin color, i.e. phototype.

Among black people, hyperpigmentation is visualized by a spotted and uneven skin. It may be the result of immune system activity in response to inflammation, infection and/or healing but also of daily use of topical products containing substances lightening, now banned in cosmetics, such as hydroquinone and/or topical corticosteroids.

In order to reduce these dermatoses, understanding the mechanisms of melanogenesis is essential. Thus, it will be easier to visualize where the potential inhibitor will act to stop and/or reduce its production of melanin.

The melanogenic pathway is a complex process that allows the production of two different skin pigments: black-brown eumelanins and yellow to reddish pheomelanins. Tyrosinase is the key enzyme required for melanin production. Her first function is the hydroxylation of tyrosine to dihydroxyphenylalanine (DOPA), the rate-limiting step of this process. Tyrosinase allows the oxidation of DOPA to DOPAquinone. Then, two pathways can be chosen.

In the absence of thiol compounds (cysteine) (Black population), DOPAquinone is oxidized spontaneously to dopachrome, a red intermediate product. This latter can cyclize spontaneously to give 5,6-dihydroxyindole (DHI), a black insoluble molecule, or be converted into 5,6-dihydroxyindole-2-carboxylic-acid (DHICA) in the presence of a second enzyme: Tyrosinase-Related-Protein 2 (TRP-2). This second intermediate must be in the presence of a DHICA oxidase activity to be converted into DHICA-melanins. This activity is ported by Tyrosinase-Related-Protein 1 (TRP-1).

Using skin bleaching cosmetics has been a social practice for about 30 years in the black female population. Today, this concept is spreading on men in certain countries in central Africa. Currently, 60% of black African women admit to use skin lightening products in order to obtain a clearer and more uniform complexion. This practice, initiated by the media, may not only cause significant dermatological complications but also systemic complications in the long run. About 70% of users have skin problems such as keloid acne, trophic disorders, hyperpigmentation, etc. These further complications, foremost dermatologic in the first time, come from the toxic activity of the compounds present in lightener products such as hydroquinone or mercury derivatives.

Currently, in France and in Africa, the most active substances used are hydroquinone, often at high concentrations exceeding 4% and topical corticosteroids with strong activity, such as clobetasol propionate at 0.05%, which is one of the most potent topical corticosteroids. These products are used in the form of creams (hydroquinone or steroids), gels (corticosteroids) or milk (hydroquinone). The amount of active substance is often indicated but may be imprecise. The use of mercuray derivatives, previously widespread seems to be more limited today. They may be used in the form of soaps called "antiseptic".

A prospective, descriptive study has been performed over a 6-month period in Senegal including 86 female patients with a mean age of 29-34 years-old (range 16-49 years-old). The break-down by skin-bleaching products showed that topical corticosteroids were the most frequently used (78%), followed by hydroquinone (56%), products based on vegetable extracts (31.7%), caustic products (8.5%) and finally, products of unknown composition (41.4%). Two components or more are frequently combined (86.5%).

Of the 19 types of complications listed, dyschromia, including hyperpigmentation of the joints, was clearly the most common. This remains a significant stigma associated with artificial depigmentation, with 85.4% sensitivity. Striae atrophicae (72%) and skin atrophy (52.4%) were also very common, testifying to the very frequent use of corticosteroids.

Moreover, since several years, evidences demonstrating that there are links between the production of reactive oxygen species (ROS) and melanin overproduction have been well described in the literature. Indeed, UV stimulation induces melanin production which in turn provokes ROS or $H_2O_2$ release in the skin leading to skin aging. Some flavonoid compounds are also known for their properties able to both inhibit melanin and ROS production (For review: GILLBRO & OLSSON, *Int. J. Cosmet. Sci.*, vol. 33(3):210-21, 2011) Thus, the identification of tyrosinase or TRP-1 inhibitors may have an interest for treating skin aging.

Thus, there remains a need in the art for substances and cosmetic compositions able to regulate the melanogenesis pathway without side effect for black and mixed skin (phototype IV-VI).

SUMMARY OF THE INVENTION

The inventors have focused on finding novel tyrosinase inhibitors to level the DOPA oxidase activity of tyrosinase and the DHICA oxidase activity of TRP-1. They have surprisingly found that some venoms, particularly spider venoms, contain this DOPA oxidase-inhibiting activity and DHICA oxidase-inhibiting activity. In addition, the inventors have isolated from a venom of spider a molecule having both DOPA oxidase-inhibiting activity and DHICA-oxidase inhibiting activity.

Now, these spider venoms activities were not known nor suggested in the prior art.

Almost, venoms from bee were disclosed in patent application KR 2010-2264 as cosmetic agent including skin whitening activity.

A first object of the invention relates to a topical composition comprising spider venoms, molecules or synthetics analogs thereof.

Another object of the invention relates to the use of spider venoms, molecules or synthetics analogs thereof as a skin whitening/depigmenting cosmetic agent.

Another object of the invention relates to a composition comprising spider venoms, molecules or synthetics analogs thereof as defined in the invention for treating and/or preventing hyperpigmentation such as melasma, chloasma, lentigines, vitiligo, post-inflammatory hyperpigmentation due to an abrasion, a burn, a scar, a dermatosis, a contact allergy, naevi, hyperpigmentation with a genetic determinism, hyperpigmentation of metabolic or drug origin, melanomas or any other hyperpigmentary lesions.

Finally, the invention relates to a non-therapeutic method for whitening/depigmenting human skin comprising the step of topically applying an effective amount on said human skin of spider venoms, molecules or synthetics analogs thereof as defined in the invention.

DETAILED DESCRIPTION OF THE INVENTION

Figure 1:
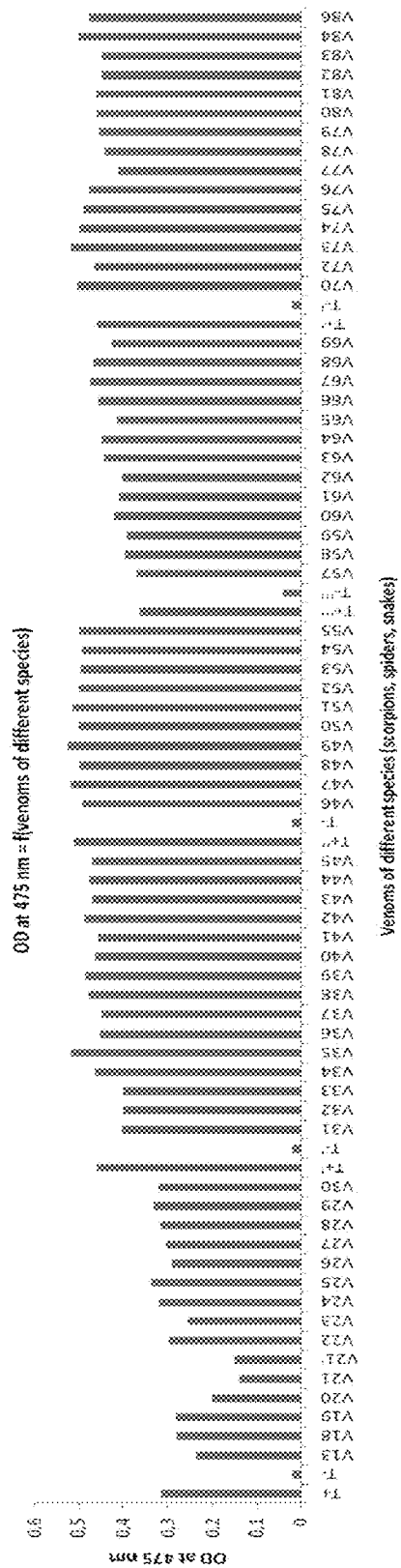
FIG. 1 shows the absorbance and thus the inhibiting activity obtained with 68 venoms extracted from different animals (scorpions, spiders, snakes).

A first object of the invention relates to a topical composition comprising spider venoms, molecules or synthetics analogs thereof.

As used herein, the term "topical composition" refers to a composition that is applied externally to any part of the body excluding mucous membranes such as the eyes, mouth, and so on. The topical composition may, therefore, be applied to any part of the body excluding mucous membranes such as the eyes, mouth, and so on. However, the topical composition of the invention may also be incorporated into sponges, swabs, pads and or wipes, which are the used to apply the topical composition to any part of the body excluding mucous membranes such as the eyes, mouth, and so on.

As used herein, the term "spider venom" refers to molecules produced by spiders and injected into their victims by the means of a bite, sting or other sharp body feature, to kill or paralyze them. Such molecules of the venoms comprise but are not limited to neurotoxins, cytolysins and hemolysins.

As used herein, the term "molecule" refers to a compound purified from the venom of a spider (e.g. by HPLC) or to a compound present in a spider venom extract.

The term "extract" as used herein refers to a substance extracted to a natural product, regardless of the extraction method or the composition of the ingredients. For example, it includes one obtained by extracting soluble ingredients from a natural product using water or an organic solvent, or one obtained by extracting only specific ingredients, such as oil, from a natural product.

As used herein, the term "synthetic analog" refers to any chemical or biological compound derived from an active molecule of venom.

As used herein, the term "analog" refers to a chemical compound that is structurally similar to another but differs slightly in composition. Thus an analog is a compound that is similar to or comparable in function and appearance to the reference compound.

Another object of the invention relates to the use of spider venoms, molecules or synthetics analogs thereof as a skin whitening/depigmenting cosmetic agent.

As used herein, the term "skin whitening agent" refers to any compound or substance that have the effect of altering the pigment of the skin as long as the agent has anti-tyrosinase activity and/or anti-melanogenesis activity.

As used herein, the term "depigmenting" or "depigmentation" refers to the reduction of the pigmentation of the skin that already exists and/or also to the prevention of any additional pigmentation greater to the natural pigmentation. For example, depigmentation is obtained by reducing the formation or rate of formation of melanin.

In a preferred embodiment, the spider venoms are chosen among venoms of spiders belonging to the genus *Lycosa*, *Argiope* or *Araneus*, preferably *Argiope* or *Araneus*.

According to *The World Spider Catalog* 12.5, the genus *Argiope* consists in the following species:

*Argiope acuminata, Argiope aemula, Argiope aetherea, Argiope aetheroides, Argiope ahngeri, Argiope amoena, Argiope anasuja, Argiope anomalopalpis, Argiope appensa, Argiope argentata, Argiope aurantia, Argiope aurocincta, Argiope australis, Argiope blanda, Argiope boesenbergi, Argiope bougainvilla, Argiope bruennichi, Argiope brunnescantia, Argiope buehleri, Argiope bullocki, Argiope caesarea, Argiope caledonia, Argiope cameloides, Argiope catenulata, Argiope chloreis, Argiope comorica, Argiope coquereli, Argiope dang, Argiope dietrichae, Argiope doboensis, Argiope ericae, Argiope flavipalpis, Argiope florida, Argiope halmaherensis, Argiope intricata, Argiope jinghongensis, Argiope katherina, Argiope keyserlingi, Argiope kochi, Argiope legionis, Argiope levii, Argiope lobata,*

*Argiope luzona, Argiope macrochoera, Argiope madang, Argiope magnifica, Argiope maja, Argiope mangal, Argiope manila, Argiope mascordi, Argiope minuta, Argiope modesta, Argiope niasensis, Argiope ocula, Argiope ocyaloides, Argiope pentagona, Argiope perforata, Argiope picta, Argiope ponape, Argiope possoica, Argiope probata, Argiope protensa, Argiope pulchella, Argiope pulchelloides, Argiope radon, Argiope ranomafanensis, Argiope reinwardti, Argiope sapoa, Argiope savignyi, Argiope sector, Argiope takum, Argiope tapinolobata, Argiope taprobanica, Argiope thai, Argiope trifasciata, Argiope truk, Argiope versicolor, Argiope vietnamensis* and *Argiope furva.*

According to *The World Spider Catalog* 13.0, the genus *Araneus* consists in the following species:

*Araneus aballensis, Araneus abeicus, Araneus abigeatus, Araneus acachmenus, Araneus acolla, Araneus acrocephalus, Araneus acronotus, Araneus acropygus, Araneus acuminatus, Araneus acusisetus, Araneus adiantiformis, Araneus adjuntaensis, Araneus aethiopicus, Araneus aethiopissa, Araneus affinis, Araneus agastus, Araneus akakensis, Araneus aksuensis, Araneus albabdominalis, Araneus albiaculeis, Araneus albidus, Araneus albilunatus, Araneus albomaculatus, Araneus alboquadratus, Araneus albotriangulus, Araneus alboventris, Araneus alhue, Araneus allani, Araneus alsine, Araneus altitudinum, Araneus amabilis, Araneus amblycyphus, Araneus amurius, Araneus amygdalaceus, Araneus ana, Araneus anantnagensis, Araneus anaspastus, Araneus anatipes, Araneus ancurus, Araneus andrewsi, Araneus anguinifer, Araneus angulatus, Araneus anjonensis, Araneus annuliger, Araneus annulipes, Araneus apache, Araneus apiculatus, Araneus apobleptus, Araneus appendiculatus, Araneus apricus, Araneus aragua, Araneus aralis, Araneus arenaceus, Araneus arfakianus, Araneus arganicola, Araneus argentarius, Araneus arizonensis, Araneus asiaticus, Araneus aubertorum, Araneus aurantiifemuris, Araneus auriculatus, Araneus axacus, Araneus badiofoliatus, Araneus badongensis, Araneus bagamoyensis, Araneus baicalicus, Araneus balanus, Araneus bandelieri, Araneus bantaengi, Araneus bargusinus, Araneus basalteus, Araneus bastarensis, Araneus baul, Araneus beebei, Araneus beijiangensis, Araneus biapicatifer, Araneus bicavus, Araneus bicentenarius, Araneus bigibbosus, Araneus bihamulus, Araneus bilunifer, Araneus bimaculicollis, Araneus bimini, Araneus biprominens, Araneus bipunctatus, Araneus bispinosus, Araneus bivittatus, Araneus blaisei, Araneus blochmanni, Araneus blumenau, Araneus boerneri, Araneus boesenbergi, Araneus bogotensis, Araneus boneti, Araneus bonsallae, Araneus borealis, Araneus boreus, Araneus bosmani, Araneus bradleyi, Araneus braueri, Araneus brisbanae, Araneus bryantae, Araneus bufo, Araneus caballo, Araneus calusa, Araneus camilla, Araneus canacus, Araneus canalae, Araneus canestrinii, Araneus caplandensis, Araneus carabellus, Araneus carchi, Araneus cardioceros, Araneus carimagua, Araneus carnifex, Araneus carroll, Araneus castilho, Araneus catillatus, Araneus catospilotus, Araneus caudifer, Araneus cavaticus, Araneus celebensis, Araneus cercidius, Araneus cereolus, Araneus chiapas, Araneus chiaramontei, Araneus chingaza, Araneus chunhuaia, Araneus chunlin, Araneus cingulatus, Araneus circe, Araneus circellus, Araneus circulissparsus, Araneus circumbasilaris, Araneus coccinella, Araneus cochise, Araneus cohnae, Araneus colima, Araneus colubrinus, Araneus compsus, Araneus comptus, Araneus concepcion, Araneus concinnus, Araneus concoloratus, Araneus corbita, Araneus corporosus, Araneus corticaloides, Araneus corticarius, Araneus crinitus, Araneus crispulus, Araneus cristobal, Araneus cuiaba, Araneus cungei, Araneus cyclops, Araneus cyphoxis, Araneus cyrtarachnoides, Araneus daozhenensis, Araneus dayongensis, Araneus decaisnei, Araneus decentellus, Araneus decolor, Araneus decoratus, Araneus demoniacus, Araneus depressatulus, Araneus desierto, Araneus detrimentosus, Araneus diabrosis, Araneus diadematoides, Araneus diadematus, Araneus dianiphus, Araneus diffinis, Araneus dimidiatus, Araneus diversicolor, Araneus doenitzellus, Araneus dofleini, Araneus dospinolongus, Araneus dreisbachi, Araneus drygalskii, Araneus ealensis, Araneus eburneiventris, Araneus eburnus, Araneus ejusmodi, Araneus elatatus, Araneus elizabethae, Araneus ellipticus, Araneus elongatus, Araneus emmae, Araneus enucleatus, Araneus enyoides, Araneus excavatus, Araneus expletus, Araneus exsertus, Araneus falcatus, Araneus fastidiosus, Araneus favorabilis, Araneus faxoni, Araneus fengshanensis, Araneus ferganicus, Araneus ferrugineus, Araneus fictus, Araneus finneganae, Araneus fishoekensis, Araneus fistulosus, Araneus flagelliformis, Araneus flavisternis, Araneus flavopunctatus, Araneus flavosellatus, Araneus flavosignatus, Araneus flavus, Araneus floriatus, Araneus formosellus, Araneus frio, Araneus fronki, Araneus frosti, Araneus fulvellus, Araneus fuscinotus, Araneus gadus, Araneus galero, Araneus gazerti, Araneus geminatus, Araneus gemma, Araneus gemmoides, Araneus gerais, Araneus gestrellus, Araneus gestroi, Araneus gibber, Araneus ginninderranus, Araneus goniaeoides, Araneus goniaeus, Araneus graemii, Araneus granadensis, Araneus granti, Araneus gratiolus, Araneus groenlandicola, Araneus grossus, Araneus guandishanensis, Araneus guatemus, Araneus guerrerensis, Araneus guessfeldi, Araneus gundlachi, Araneus gurdus, Araneus guttatus, Araneus guttulatus, Araneus habilis, Araneus haematomerus, Araneus hamiltoni, Araneus hampei, Araneus haploscapellus, Araneus haruspex, Araneus herbeus, Araneus hierographicus, Araneus himalayanus, Araneus hirsti, Araneus hirsutulus, Araneus hispaniola, Araneus holzapfelae, Araneus horizonte, Araneus hortensis, Araneus hoshi, Araneus hotteiensis, Araneus huahun, Araneus hui, Araneus huixt/a, Araneus humilis, Araneus idoneus, Araneus iguacu, Araneus illaudatus, Araneus indistinctus, Araneus inquietus, Araneus interjectus, Araneus inustus, Araneus iriomotensis, Araneus isabella, Araneus ishisawai, Araneus iviei, Araneus jalimovi, Araneus jalisco, Araneus jamundi, Araneus juniperi, Araneus kalaharensis, Araneus kapiolaniae, Araneus karissimbicus, Araneus kerr, Araneus kirgisikus, Araneus kiwuanus, Araneus klaptoczi, Araneus koepckeorum, Araneus komi, Araneus kraepelini, Araneus lacrymosus, Araneus ladschicola, Araneus lamperti, Araneus lancearius, Araneus IanioAraneus, lateriguttatus Araneus, lathyrinus Araneus latirostris, Araneus leai, Araneus lechugalensis, Araneus legonensis, Araneus lenkoi, Araneus lenzi, Araneus leones, Araneus liae, Araneus liber, Araneus liberalis, Araneus liberiae, Araneus licenti, Araneus lineatipes, Araneus lineatus, Araneus linshuensis, Araneus lintatus, Araneus linzhiensis, Araneus lithyphantiformis, Araneus lixicolor, Araneus loczyanus, Araneus lodicula, Araneus longicaudus, Araneus luteofaciens, Araneus lutulentus, Araneus macacus, Araneus macleayi, Araneus madagascaricus, Araneus mamillanus, Araneus mammatus, Araneus mangarevoides, Araneus margaritae, Araneus margitae, Araneus mariposa, Araneus marmoreus, Araneus marmoroides, Araneus masculus, Araneus masoni, Araneus mastersi, Araneus matogrosso, Araneus mauensis, Araneus mayumiae, Araneus mazamitla, Araneus mbogaensis, Araneus memoryi, Araneus mendoza, Araneus menglunensis, Araneus meropes, Araneus mertoni, Araneus metalis, Araneus metellus, Araneus meus, Araneus miami, Araneus microsoma, Araneus microtuberculatus,*

*Araneus mimosicola, Araneus minahassae, Araneus miniatus, Araneus minutalis, Araneus miquanensis, Araneus missouri, Araneus mitificus, Araneus monica, Araneus monoceros, Araneus montereyensis, Araneus moretonae, Araneus mortoni, Araneus morulus, Araneus mossambicanus, Araneus motuoensis, Araneus mulierarius, Araneus musawas, Araneus myurus, Araneus nacional, Araneus nashoba, Araneus necopinus, Araneus neocaledonicus, Araneus nephelodes, Araneus nidus, Araneus nigmanni, Araneus nigricaudus, Araneus nigrodecoratus, Araneus nigroflavornatus, Araneus nigromaculatus, Araneus nigropunctatus, Araneus nigroquadratus, Araneus niveus, Araneus noegeatus, Araneus nojimai, Araneus nordmanni, Araneus nossibeus, Araneus notacephalus, Araneus notandus, Araneus noumeensis, Araneus novaepommerianae, Araneus nox, Araneus nuboso, Araneus nympha, Araneus obscurissimus, Araneus obscurtus, Araneus obtusatus, Araneus ocaxa, Araneus ocellatulus, Araneus octodentalis, Araneus octumaculalus, Araneus ogatai, Araneus omnicolor, Araneus orgaos, Araneus origenus, Araneus oxygaster, Araneus oxyurus, Araneus paenulatus, Araneus pahalgaonensis, Araneus pahli, Araneus paitaensis, Araneus pallasi, Araneus pallescens, Araneus pallidus, Araneus panchganiensis, Araneus panniferens, Araneus papulatus, Araneus partitus, Araneus parvulus, Araneus parvus, Araneus pauxillus, Araneus pavlovi, Araneus pecuensis, Araneus pegnia, Araneus pellax, Araneus penal, Araneus pentagrammicus, Araneus perincertus, Araneus petersi, Araneus pfeifferae, Araneus phaleratus, Araneus phlyctogena, Araneus phyllonotus, Araneus pichoni, Araneus pico, Araneus pictithorax, Araneus pinguis, Araneus pistiger, Araneus pius, Araneus plenus, Araneus pogisa, Araneus poltyoides, Araneus polydentatus, Araneus pontii, Araneus popaco, Araneus postilena, Araneus poumotuus, Araneus praedatus, Araneus praesignis, Araneus prasius, Araneus pratensis, Araneus principis, Araneus pronubus, Araneus prospiciens, Araneus providens, Araneus prunus, Araneus pseudoconicus, Araneus pseudosturmii, Araneus pseudoventricosus, Araneus psittacinus, Araneus pudicus, Araneus puebla, Araneus pulcherrimus, Araneus pulchriformis, Araneus punctipedellus, Araneus pupulus, Araneus purus, Araneus qianshan, Araneus quadratus, Araneus quietus, Araneus quirapan, Araneus rabiosulus, Araneus radja, Araneus ragnhildae, Araneus rainbowi, Araneus ramulosus, Araneus rani, Araneus rarus, Araneus raui, Araneus recherchensis, Araneus relicinus, Araneus repetecus, Araneus riveti, Araneus roseomaculatus, Araneus rotundicornis, Araneus rotundulus, Araneus royi, Araneus rubicundulus, Araneus rubripunctatus, Araneus rubrivitticeps, Araneus rufipes, Araneus russicus, Araneus ryukyuanus, Araneus saccalava, Araneus saevus, Araneus sagicola, Araneus salto, Araneus sambava, Araneus santacruziensis, Araneus santarita, Araneus savesi, Araneus schneblei, Araneus schrencki, Araneus scutellatus, Araneus scutifer, Araneus scutigerens, Araneus selva, Araneus seminiger, Araneus senicaudatus, Araneus separatus, Araneus septemtuberculatus, Araneus sericinus, Araneus sernai, Araneus shunhuangensis, Araneus sicki, Araneus simillimus, Araneus singularis, Araneus sinistrellus, Araneus sinuosus, Araneus sogdianus, Araneus spathurus, Araneus speculabundus, Araneus sponsus, Araneus squamifer, Araneus stabilis, Araneus stella, Araneus stolidus, Araneus strandiellus, Araneus striatipes, Araneus strigatellus, Araneus strupifer, Araneus sturmi, Araneus suavis, Araneus subflavidus, Araneus subumbrosus, Araneus sulfurinus, Araneus svanetiensis, Araneus sydneyicus, Araneus sylvicola, Araneus taigunensis, Araneus talasi, Araneus talca, Araneus talipedatus, Araneus tambopata, Araneus tamerlani, Araneus taperae, Araneus tartaricus, Araneus tatianae, Araneus tatsulokeus, Araneus tellezi, Araneus tenancingo, Araneus tenerius, Araneus tengxianensis, Araneus tepic, Araneus tetraspinulus, Araneus texanus, Araneus thaddeus, Araneus thevenoti, Araneus thorelli, Araneus tiganus, Araneus tijuca, Araneus tinikdikitus, Araneus titirus, Araneus toma, Araneus tonkinus, Araneus toruaigiri, Araneus transversivittiger, Araneus transversus, Araneus triangulus, Araneus tricoloratus, Araneus trifolium, Araneus trigonophorus, Araneus triguttatus, Araneus tschuiskii, Araneus tsurusakii, Araneus tubabdominus, Araneus tuscarora, Araneus ubicki, Araneus unanimus, Araneus uniformis, Araneus unistriatus, Araneus urbanus, Araneus urquharti, Araneus ursimorphus, Araneus uruapan, Araneus urubamba, Araneus usualis, Araneus uyemurai, Araneus variegatus, Araneus venatrix, Araneus ventricosus, Araneus ventriosus, Araneus vermimaculatus, Araneus villa, Araneus vincibilis, Araneus viperifer, Araneus virgunculus, Araneus virgus, Araneus viridisomus, Araneus, viridiventris, Araneus viridulus, Araneus v-notatus, Araneus volgeri, Araneus vulpinus, Araneus vulvarius, Araneus walesianus, Araneus washingtoni, Araneus wokamus, Araneus woodfordi, Araneus workmani, Araneus wulongensis, Araneus xavantina, Araneus xianfengensis, Araneus xizangensis, Araneus yadongensis, Araneus yapingensis, Araneus yasudai, Araneus yatei, Araneus yuanminensis, Araneus yukon, Araneus yunnanensis, Araneus yuzhongensis, Araneus zapallar, Araneus zebrinus, Araneus zelus, Araneus zhangmu, Araneus zhaoi, Araneus zuluanus, Araneus zygielloides, Araneus absconditus, Araneus aethus, Araneus beipiaoensis, Araneus carbonaceous, Araneus cinefactus, Araneus defunctus, Araneus delitus, Araneus emertoni, Araneus exustus, Araneus kinchloeae, Araneus inelegans, Araneus leptopodus, Araneus liaoxiensis, Araneus longimanus, Araneus longipes, Araneus luianus, Araneus meeki, Araneus molassicus, Araneus nanus, Araneus piceus, Araneus reheensis, Araneus ruidipedalis, Araneus troschelii* and *Araneus vulcanalis*.

According to *The World Spider Catalog* 14.0, the genus *Lycosa* comprises the following species:

*Lycosa abnormis, Lycosa accurata, Lycosa adusta, Lycosa affinis, Lycosa ambigua, Lycosa anclata, Lycosa apacha, Lycosa approximata, Lycosa arambagensis, Lycosa ariadnae, Lycosa articulata, Lycosa artigas, i Lycosa asiatica, Lycosa aurea, Lycosa auroguttata, Lycosa australicola, Lycosa australis, Lycosa balaramai, Lycosa barnesi, Lycosa bedeli, Lycosa beihaiensis, Lycosa bezzii, Lycosa bhatnagari, Lycosa biolleyi, Lycosa bistriata, Lycosa boninensis, Lycosa bonneti, Lycosa brunnea, Lycosa caenosa, Lycosa canescens, Lycosa capensis, Lycosa carbonelli, Lycosa carmichaeli, Lycosa cerrofloresiana, Lycosa chaperi, Lycosa choudhuryi, Lycosa cingara, Lycosa clarissa, Lycosa coelestis, Lycosa connexa, Lycosa contestata, Lycosa corallina, Lycosa coreana, Lycosa cowlei, Lycosa cretacea, Lycosa dacica, Lycosa danjiangensis, Lycosa dilatata, Lycosa dimota, Lycosa discolor, Lycosa elysae, Lycosa emuncta, Lycosa erjianensis, Lycosa erythrognatha, Lycosa eutypa, Lycosa falconensis, Lycosa fernandezi, Lycosa ferriculosa, Lycosa formosana, Lycosa frigens, Lycosa fuscana, Lycosa futilis, Lycosa geotubalis, Lycosa gibsoniLycosa gigantea, Lycosa howarthi, Lycosa insularis, Lycosa lambai, Lycosa langei, Lycosa lativulva, Lycosa lebakensis, Lycosa leireana, Lycosa leuckarti, Lycosa leucogastra, Lycosa leucophaeoides, Lycosa leucophthalma, Lycosa leucotaeniata, Lycosa liliputana, Lycosa longivulva, Lycosa mordax, Lycosa nordenskjoldi, Lycosa philadelphiana, Lycosa prolifica, Lycosa similis, Lycosa singoriensis* and *Lycosa yunnanensis*. In a preferred embodiment, the spider venoms are chosen among *Argiope Lobata, Argiope Bruennichi, Araneus tartaricus, Araneus Cornutus* and *Lycosa Singoriensis* venoms; most preferably among *Argiope Lobata, Argiope Bruennichi*, and *Araneus tartaricus*.

*Argiope lobata* is a species of spider belonging to the family of Araneidae. It has a wide distribution encompassing the whole Africa and stretching to southern Europe and into Asia.

*Argiope bruennichi* is a species of spider belonging to the family of Araneidae. Its distribution encompasses central and northern Europe, northern Africa and parts of Asia.

*Araneus tartaricus* is a species of spider belonging to the family of Araneidae. It is found in western Asia.

*Araneus cornutus* is a species of spider belonging to the family of Araneidae. It is predominantly found in Europe, North of America and western Asia.

*Lycosa Singoriensis* is a species of spider belonging to the family of Lycosidae. It is predominantly found in central Europe. In a preferred embodiment, the spider venom of the invention is the venom of *Argiope Lobata*.

In a preferred embodiment, the spider venom molecule or synthetic analog of the invention is represented by formula (1).

$$R1-R2-R3-R4-R5-R6 \quad (1)$$

wherein

R1 is an H or an aromatic such as $(OH)_2C_6H_3$—$CH_2$—$C(=O)$— or tyrosine;

R2 is —NH—CH[$(CH_2)_n$—$C(=O)$—$NH_2$]—$C(=O)$—, with n=1 or 2, preferably n=1 (i.e. R2 is asparagine);

R3 is —NH—$(CH_2)_{n'}$—NH—, with n' is an integer between 1 and 7, preferably between 1 and 6, and most preferably n'=5;

R4 is absent or is —$(CH_2)_{n''}$—NH—, with n'' is an integer between 1 and 7, preferably n''=3 or 4, and still preferably n''=3;

R5 is absent or is —$(CH_2)_{n'''}$—NH—, with n''' is an integer between 1 and 7, preferably n'''=3 or 4, and still preferably n'''=3;

R6 is an arginine residue; and

R1, R2, R3, R5 or R6 can be modify so that each peptide link R1-R2, R2-R3 or R5-R6 may be independently replaced by a bond selected in the group comprising —CH2-CH2-, —CH=CH—, —C(=O)—CH2-, —CH2-S—, —CH2-NH, —CH2-O—, —CH(OH)—CH2-, or —CH2-SO—.

In another preferred embodiment, the spider venom molecule is the represented by formula (2)

In a preferred embodiment, the use of the whitening/depigmenting cosmetic agent of the invention is for preventing and/or treating photo-induced or chronologic signs of aging of the skin.

As used herein, the term "photo-induced signs of aging" refers to the extrinsic aging of the skin, caused by the sun and more particularly by ultraviolet rays, which induce an increase in free radicals and oxidative stress in the dermis.

As used herein, the term "chronologic signs of aging" refers to intrinsic aging of the skin, caused by genetic and metabolic and leading to a progressive atrophy and degeneration of the dermis, hypodermis and support structures of the skin.

Another object of the invention relates to a composition comprising spider venoms, molecule or synthetic analog thereof as defined in the invention for treating and/or preventing hyperpigmentation such as melasma, chloasma, lentigines, vitiligo, post-inflammatory hyperpigmentation due to an abrasion, a burn, a scar, a dermatosis, a contact allergy, naevi, hyperpigmentation with a genetic determinism, hyperpigmentation of metabolic or drug origin, melanomas or any other hyperpigmentary lesions.

As used herein, the term "treating" means to cure an already present disease state or condition in a patient or subject. Treating can also include arresting the development of a disease state or condition, and relieving or ameliorating, i.e. causing regression of the disease state or condition.

The term "preventing", as used herein, means to completely or almost completely stop a disease state or condition from occurring in a patient or subject, especially when the patient or subject is predisposed to such or at risk of contracting a disease state or condition. Preventing can also include arresting the development of a disease state or condition.

As used herein, the term "hyperpigmentation" refers to a range of skin disorders caused by an increased production of melanin and results in localized areas of increase skin pigmentation. Hyperpigmentation can refer to regional hyperpigmentation due to melanocytic hyperactivity, such as idiopathic melasma, to localized hyperpigmentation due to benign melanocytic hyperactivity and proliferation, such as senescent pigmentary blemishes (senile lentigo), and to accidental hyperpigmentation, such as photo-sensitization or cicatricial hyperpigmentation, and for the treatment of certain leukodermias, such as vitiligo.

Finally, the invention relates to a non-therapeutic method for whitening/depigmenting human skin comprising the step (2)

Said compound of formula (2) called Argiotoxin-636, also known as argiopine, is a polyamine isolated from the venom of *A. lobata*. (CHEMBL 1098240, CHEBI 724404).

of topically applying an effective amount on said human skin of spider venoms, molecules or synthetic analogs thereof as defined in the invention.

As used herein, the term "effective amount" of a composition comprising an active agent means a sufficient amount of said composition to provide the desired effect.

As used herein, the term "therapeutic effect" refers to the inhibition of the abnormal condition. The term "therapeutic effect" also refers to the inhibition of factors causing or contributing to the abnormal condition. A therapeutic effect relieves to some extent one or more of the symptoms of the abnormal condition.

The followings experiments are offered to illustrate embodiments of the invention and should not be viewed as limiting the scope of the invention.

EXAMPLES

I. Material and Methods

1) In Vitro Experiments a) HPLC fractionation of venoms

Solvents were purchased from Carlo Erba (Val de Reuil, France) and venoms are obtained thanks to LATOXAN (Valence, France).

To identify the active molecules, the venoms were splitted by high pressure liquid chromatography (HPLC) in twenty fractions. HPLC was performed on a model 1100 from Hewlett Packard, the eluate absorbance was recorded at a wavelength of 214 nm and a reversed phase column (Eurospher 100 or 300-5 C18, 120*16 mm) was used. The filtered venom solutions were manually injected (FIG. 1). The solvent system (mobile phase) was: buffer A=0.1% TFA in water and buffer B=0.08% TFA in Acetonitrile 90%/water; the flow rate was 4 mL/min of 0 to 60% of buffer B in 60 min. Then, all HPLC fractions were tested to localize the inhibition of the DOPA oxidase activity. Lyophilized active fractions of venoms were then purified, the method used was the same as previously described.

b) Mushroom tyrosinase assay

Mushroom (*Agaricus bisporus*) tyrosinase (SIGMA-ALDRICH, T3824) has both DHICA oxidase and DOPA oxidase activity (SUGUMARAN et al, *Pigment Cell Res.*, vol. 12(2), p: 118-25, 1999).

The effect of different venoms, synthetic molecules and peptides on the tyrosinase activity was determined.

i. Quantification of DOPA Oxidase Inhibiting Activity by Spectrophotometry

The effect of different spider venoms on the DOPA oxidase activity was measured spectrophotometrically. The DOPA oxidase activity was determined using L-DOPA as substrate at 0.2 mM. The amount of DOPA chrome (red pigment) formed was measured against blank at 475 nm. The percentage of DOPA oxidase inhibition was obtained from:

$$\text{Inhibition percentage} = [(A-B)/(C-D)*100]$$

With:

A: Absorbance at 475 nm of the reaction medium+inhibitor sample solution with enzyme B: Absorbance at 475 nm of the reaction medium+inhibitor sample solution without enzyme (blank)

C: Absorbance at 475 nm of the reaction medium enzyme without inhibitor sample solution D: Absorbance at 475 nm of the reaction medium without both enzyme and inhibitor sample solution L-DOPA and mushroom tyrosinase (*Agaricus Bisporus*, T3824), were obtained from Sigma Aldrich (Saint Quentin Fallavier, France).

The inhibition of DOPA oxidase activity using mushroom tyrosinase was assayed in vitro as previously described by Elmer-Rico E Mojica et al. (*CitPhilippine Journal of Crop Science*, vol. 30(1), p: 47-51, 2005) with some modifications. Solutions of 1 mg/mL of mushroom tyrosinase in PBS buffer solution (137 mM NaCl, 2.7 mM KCl, 10 mM $Na_2HPO_4$, and adjust the pH to 6.8), and 0.4 mM L-dihydroxyphenylalanine (L-DOPA) were prepared.

For the DOPA activity assay: 500 µL of the L-DOPA solution at 0.4 mM is mixed with different volumes according to the different natural inhibitors at 10 mg/mL, and 5 µL of the mushroom tyrosinase solution (added last to initiate the enzymatic reaction and must be kept in ice). The final volume is 1 mL in Phosphate buffer saline (PBS) solution, pH 6.8. The absorbance is measured at 475 nm every minute for 15 min using a UV-VIS spectrophotometer BIOMATE 5®. The blank used was the sample without the enzyme solution.

To make the venom solution at 10 mg/mL, 10 mg of each venom were weighted and solubilized in 1 mL of PBS buffer solution. The solution was filtered on a 0.45 µm filter.

The Lineweaver-Burk Assay

Experimental conditions of this assay were cited above. L-DOPA was used at different concentrations (to 0.1 mM from 0.4 mM), the enzyme is the mushroom tyrosinase at 25 Units. Each point has been done in duplicate.

The DOPAchrome formation was determined by spectrophotometry at 475 nm.

ii. Quantification of DHICA Oxidase-Inhibiting Activity by MBTH Assay

DHICA is used as substrate at 0.25 mM. MBTH was obtained from Alfa Aesar and DHICA was prepared according to WAKAMATSU & ITO, (*Anal. Biochem.*, vol. 170(2), p: 335-40, 1988). Here, the MBTH method was used. This method consists to visualize the production of hydrazone-quinone adduct by spectrophotometry. The principle is that MBTH captures the indole-quinone which was generated by the oxidation of dihydroxyindole compounds. DHICA is converted to indole-5,6-quinone-2-carboxylic acid by the DHICA oxidase activity of mushroom tyrosinase, the indole product is trapped by MBTH and the complex formation can be detected at 492 nm (OLIVARES et al, *Biochem. J.*, vol. 354, p: 131-139, 2001).

c) The DHICA oxidase inhibiting activity using mushroom tyrosinase was assayed in vitro. The procedure is the same as described by WINDER & HARRIS (*Eur. J. Biochem.*, vol. 198(2), p: 317-26, 1991) for DOPA oxidase with minor modifications. Purification of the fractions The same HPLC method as described above is used. The HPLC-MS used was the LC-2010A HT Liquid Chromatograph (SHIMADZU, Marne la Vallée, France). Two different wavelengths, at 214 and 280 nm were used.

d) Molecular characterization by liquid chromatography/mass spectrometry

The mass analysis was carried out on shimadzu LCMS-2010 EV HPLC system. The mass of the interest molecule was determined using the following formula:

$$\frac{m}{z} = \frac{Mproduct + (z*Madduct)}{z}$$

Adducts products are: $m/z+H^+$ (1 g/mol), or $m/z+Na^+$ (23 g/mol), or $m/z+K^+$ (39.1 g/mol).

e) The amino acid analysis

In addition to mass spectrometry, the identity of the Argiotoxin was assessed by an amino acid analysis (AAA) after acid hydrolysis [6N HCl, 72 h, 110° C.]. All purified argiotoxin batches were quantified by this AAA method.

2) In Vivo Experiments a) Reagents

Venoms were kindly provided by LATOXAN (Valence, France). Cell culture media, trypsin-EDTA, penicillin/streptomycin were purchased from GIBCO (Saint Aubin, France). Alpha-Melanocyte Stimulating Hormone (α-MSH), 3,4-dihydoxyphenilalanine (L-DOPA) and Kojic Acid were purchased from SIGMA-ALDRICH (Saint Quentin-Falavier, France) and ALFA AESAR (Ward Hill, Mass., USA) respectively.

b) Cell Culture

B16F10 were obtained from the American Type Culture Collection (ATCC CRL-6475, Manassas, Va., USA). Cells were cultured in Dulbecco's Modified Eagle Medium (DMEM) supplemented by 10% heat-inactivated foetal bovine serum (FBS, LONZA ltd., Basel, Switzerland) and penicillin/streptomycin (50 µg/ml) in a humidified atmosphere containing 5% $CO_2$ at 37° C.

c) Cell Viability Assay

The evaluation of B16F10 cells survival relies on the reduction of the tetrazolium ring of water soluble MTT (3-[4,5-dimethylthiazol-2-yl]-2,5-diphenyltetrazolium bromide; Sigma Aldrich) into insoluble purple formazan crystals by the mitochondrial succinate dehydrogenase enzyme. The production of formazan directly reflects the number of living or dead cells. B16F10 cells were seeded at 25000 per well in a 96-well plate and incubated in standard culture condition. After 24 h of growth, the supernatant was removed and replace by fresh culture medium containing various concentration of DHPA, Argiotoxin or Kojic Acid for 6 h at 37° C. Then, the supernatant was removed and replace by 50 µl of 0.5 mg/ml of MTT solution. The cells were exposed to MTT for 2 h. Finally, each well was washed by PBS1X and the crystals contained in wells are solubilized by adding 100 µl of DMSO. After briefly shaked the plate, the absorbance is measured at 600 nm.

d) Measurement of Melanin Content in B16F10 Melanoma Cells

Determination of the extracellular melanin is considered as an index of melanogenesis. B16F10 cells were cultured in 24-well plate ($5.10^4$ cells/well) in a phenol red free medium and stimulated with 100 nM of α-MSH. Then, 24 h later, cells were incubated for 48 h with increasing concentration of DHPA (from 0 to 250 µM), Argiotoxin (from 0 to 42.1 µM) or Kojic Acid (0 to 100 µM) as a control. To quantify the amount of melanin released in the medium, the absorbance of 200 µl of supernatant was read at 405 nm. The values were normalized by the measurement of total protein level present in each well.

e) Protein Level Determination

Cells were washed with PBS1X and dissolved in 200 µl of NaOH 1N for 1 h at 60° C. The lysate was then centrifuged and the protein content determined by the Folin Lowry method, using the DC protein Assay kit from BIO-RAD (Marnes-la-Coquette, France). The absorbance is read at 475 nm.

f) Western Blot Analysis

Cells were seeded at $1.10^6$ cells/dish and cultivated in n-dish as previously described. After trypsination, the pelled were homogenized in a solution containing Sodium Dodecyl Sulphate (SDS) and were boiled 5 min at 96° C. to denature the proteins. Protein extracts were separated via a 10% SDS-PAGE for 1 h at 200 V and transferred onto a polyvinylidene difluoride membrane (GE healthcare Europe, Vélizy-villacoublay, France). The membranes were blocked overnight with 5% non-fat skim milk in a Tris-buffered saline solution containing 0.1% Tween. Membranes were incubated for 1 h at 37° C. with specific antibody against tyrosinase, TRP1 or MITF (C-19; G-17; N-15, 1:200 for Tyrosinase and TRP1 and 1:100 for MITF, Santa Cruz, Heidelberg, Germany) and actin as a control (C-11, 1:200, Santa Cruz). Membranes were incubated with secondary antibody coupled to horseradish peroxidase (HRP) for 2 h at room temperature (anti-goat 1:2500 for tyrosinase, TRP1 and MITF (ab 97120, Abcam, Paris, France) and anti-rabbit 1:2500 for actin (NA 934V, GE Healthcare)). The antibody staining was revealed by a chemiluminescent HRP substrate (Immobilon Western Kit, Milipore, Molsheim, France). Pre-stained protein markers were used for molecular weight.

g) Statistical Analysis

Statistical significance was demonstrated by the Student's t-test. The test is performed on experiences done in triplicate, quadruplicate or conducted at least 3 times independently. Values of $p<0.05$ were considered to be statistically significant and marked by one asterisk. Two asterisks reflect that p is less than 0.01.

II. Results

1) In Vitro Assays a) Venoms Screening

Sixty eight venoms extracted from different species and families of venomous animals such as snakes, scorpions, spiders, etc., have been screened using UV spectrometry. The objective is to show the potential inhibiting activity of these different venoms on DOPA oxidase activity of the mushroom tyrosinase.

Venom 21, a spider venom, has a DOPA oxidase inhibiting activity on the mushroom tyrosinase. (FIG. 1). Venom 21 shows the most interesting DOPA oxidase-inhibiting activity among the 68 venoms tested.

b) Spider Venoms Screening

Figure 2:
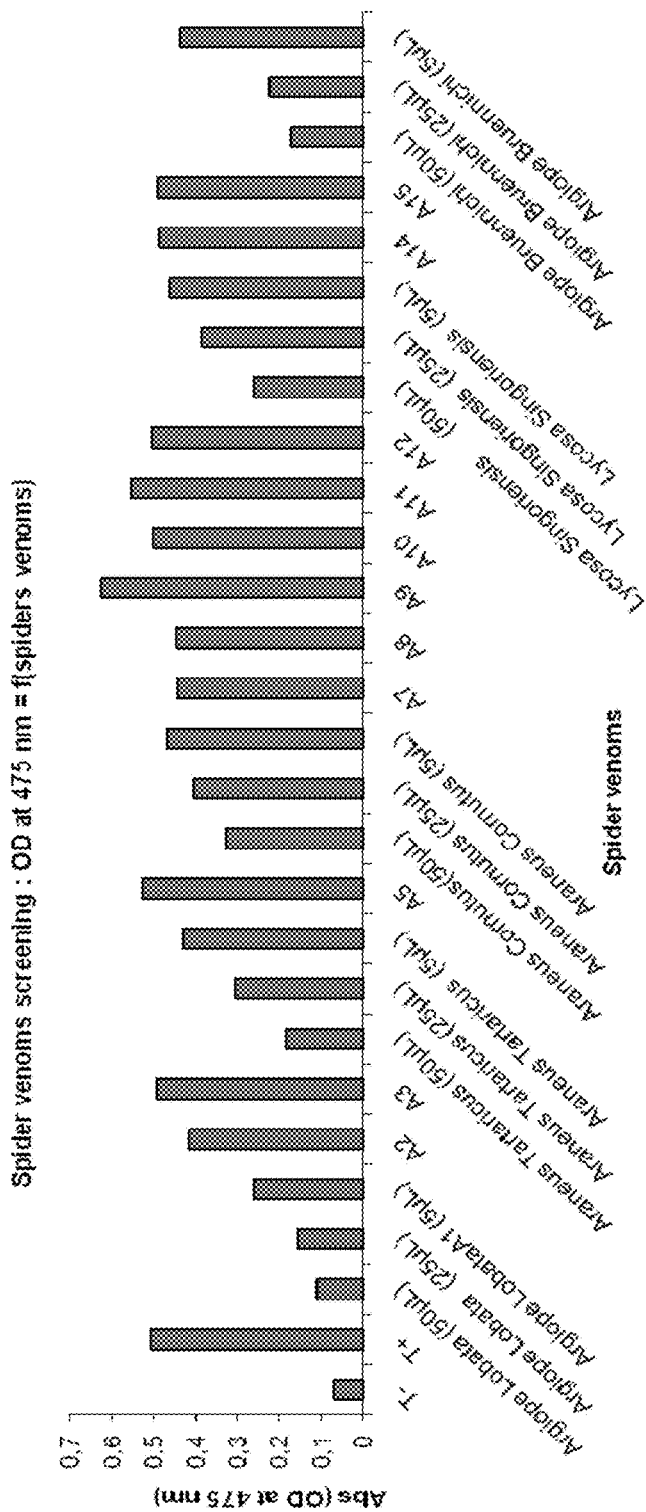
FIG. 2 shows the screening of 16 different spider venoms.

From this first screening (FIG. 1), it was found that the most active venom was the *Argiope Lobata* venom (venom 21). A second screening was performed, with only spider venoms (FIG. 2). Each initial venom solution is at 10 mg/mL, and 50 µL of them have been tested.

Figure 3:
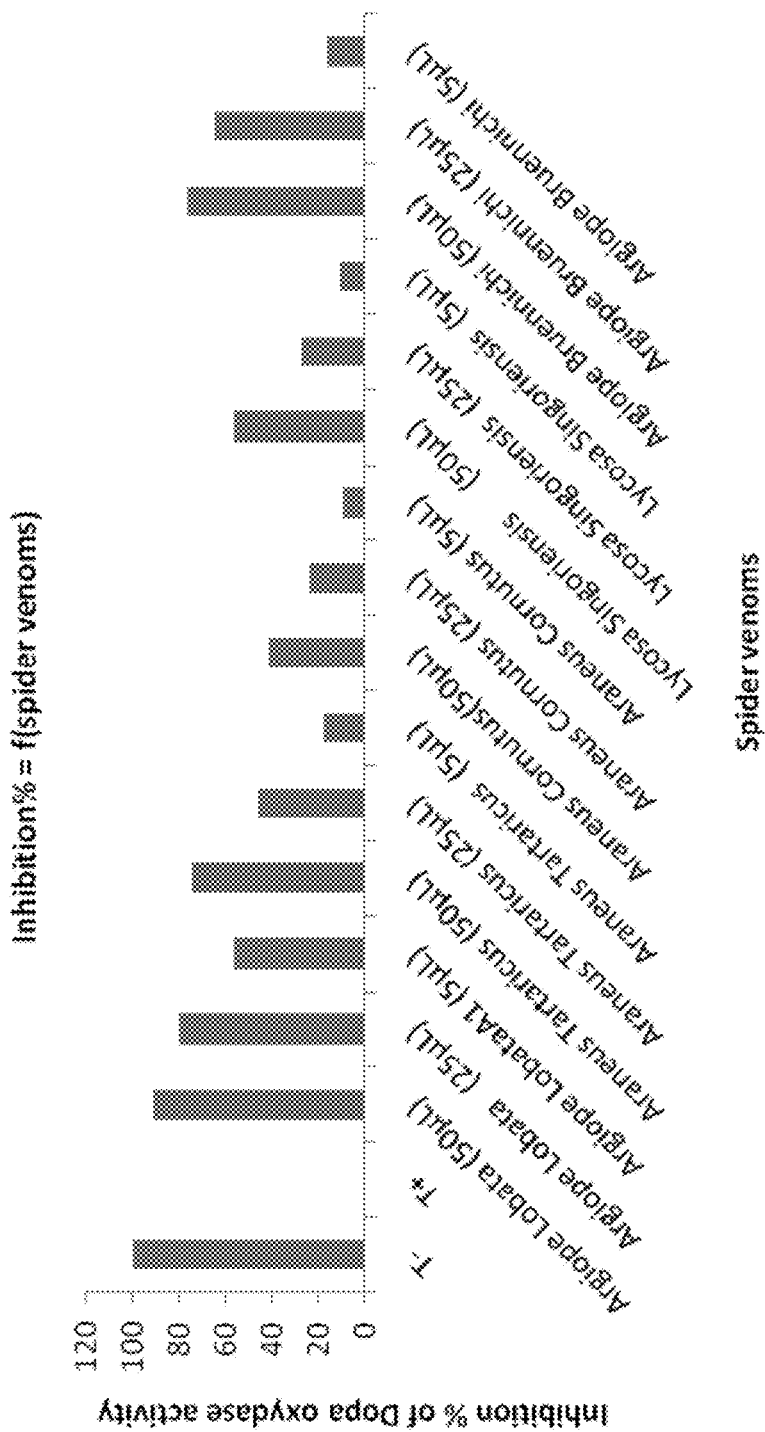
FIG. 3 shows the dose-response effects of 5 active spider venoms.

The FIG. 2 shows the results obtained with 16 spider venoms. For venoms having an inhibitory effect, a dose-response was realized (FIG. 3). Many venoms from different spider families are able to inhibit the DOPA oxydase activity. Here, *Argiope Lobata, Araneus Tartaricus, Araneus Cornutus, Lycosa Singoriensis* and *Argiope Bruennichi* are cited for their inhibitory properties.

*Argiope Lobata, Araneus Tartaricus, Araneus Cornutus, Lycosa Singoriensis* and *Argiope Bruennichi* venoms show an important DOPA oxidase-inhibiting activity because they have the lowest absorbance, compared to other spider venoms (FIG. 2). *Argiope Lobata* (50 µL) has an absorbance around 0.1 and an inhibiting activity of DOPA oxidase around 90.9%. *Araneus Tartaricus* (50 µL) has an absorbance around 0.2 and an inhibiting activity of DOPA oxidase around 74.5%. *Aranaeus Cornutus* (50 µL) has an absorbance around 0.3 and an inhibiting activity of DOPA oxidase around 41.0%. *Lycosa Singoriensis* (50 µL) has an absorbance around 0.250 and an inhibiting activity of DOPA oxidase around 56.3%. *Argiope Bruennichi* (50 µL) has an absorbance around 0.175 and an inhibiting activity of DOPA oxidase around 76.5% (FIG. 3).

Due to its higher potency among the active spider venoms, the venom extracted from *Argiope Lobata* has been further studied for its activity on melanogenesis processes.

c) Fractionation, HPLC and Mass Spectrometry Analysis of *Argiope Lobata* Venom

Fractionation of *Argiope Lobata* Venom

Figure 4:
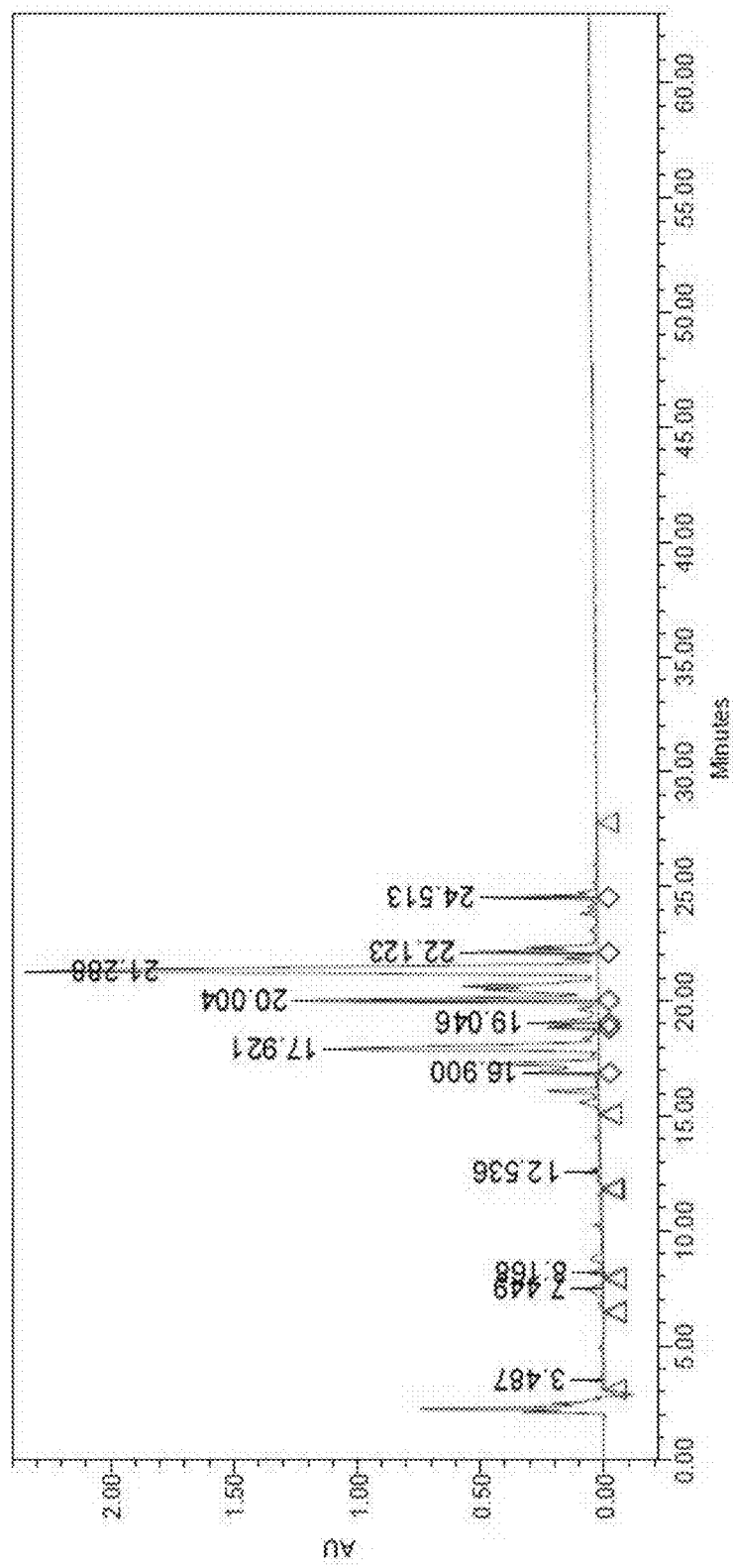
FIG. 4 shows analytical C18 reverse phase HPLC chromatogram of the filtered *Argiope Lobata* venom.

From an initial venom solution of *Argiope Lobata* venom at 7 mg/mL (FIG. 4), a fractionation in twenty equivalent fractions has been realized to localize this DOPA oxidase inhibition activity. These fractions are always tested using UV spectrophotometry. 40 μL of each fraction were lyophilized then taken in 100 μL of PBS. Only 20 μL of this latter solution is used for the spectrophotometric assay.

Figure 5:
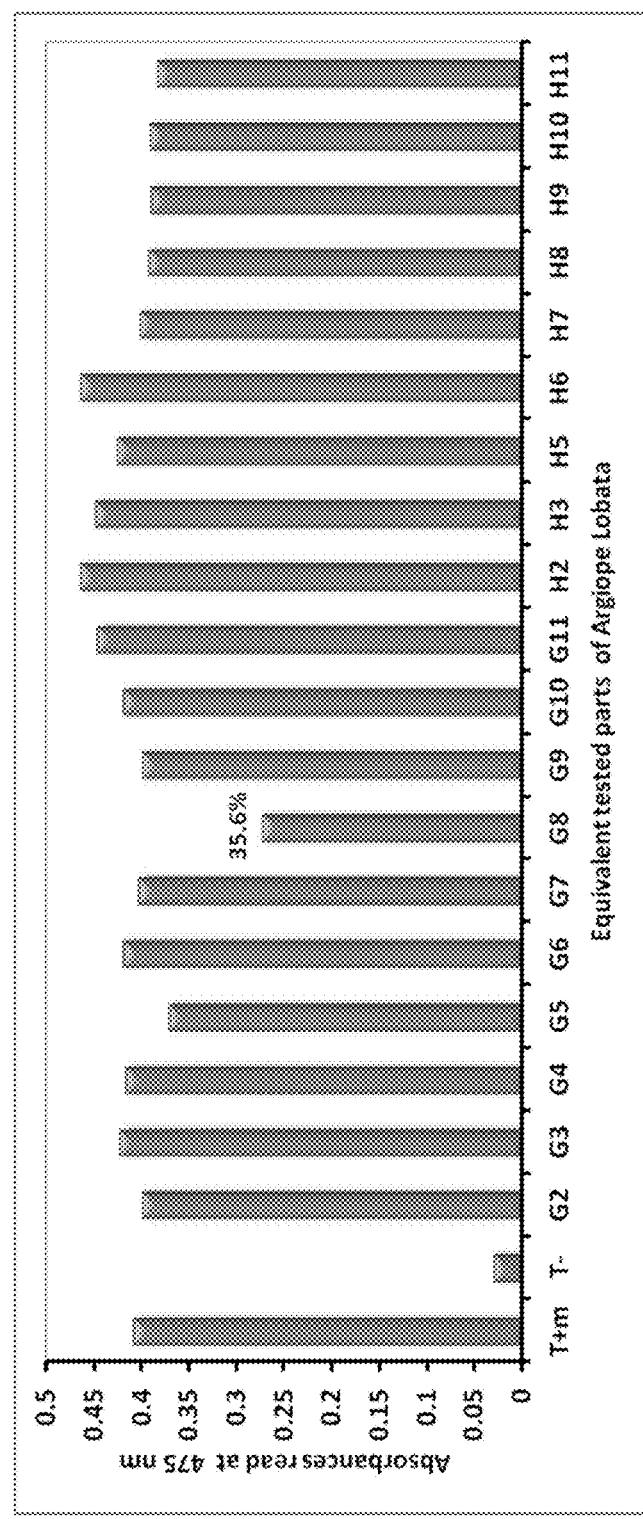
FIG. 5 shows the absorbance and thus the inhibiting activity of different equivalent fraction of *Argiope Lobata*.

FIG. 5 shows the inhibiting activity of different equivalent fractions of *Argiope Lobata* venom. The G8 fraction exhibits the lowest absorbance (about 0.25) and thus the highest inhibiting activity of DOPA oxidase activity (35.6%).

These results show that the DOPA oxidase-inhibiting activity is localized in fraction G8 of *Argiope Lobata* venom.

The purification of the fraction G8 (data not shown) of the *Argiope Lobata* venom was done by Alliance HPLC to isolate the active molecules and characterize them by mass spectrometry.

Figure 6:
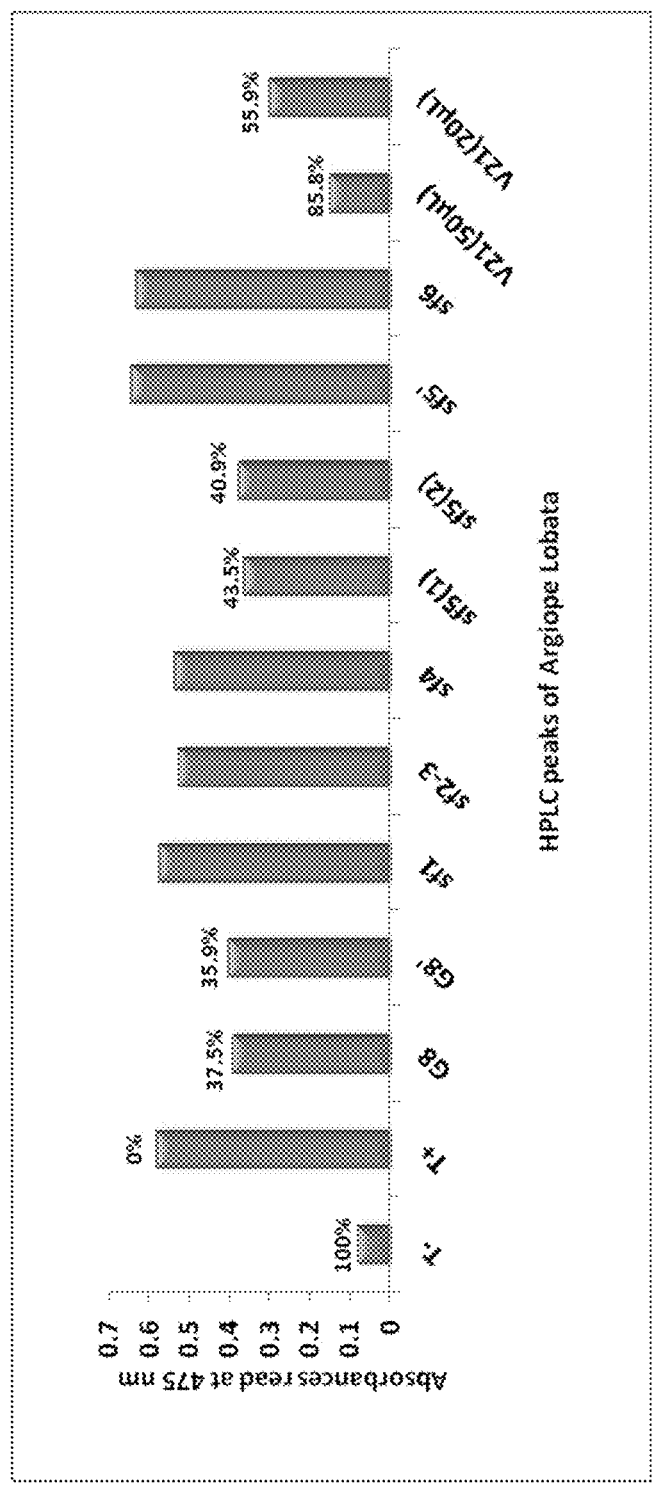
FIG. 6 shows the absorbance and thus the inhibiting activity of different HPLC peaks of *Argiope Lobata*.
Figure 7:
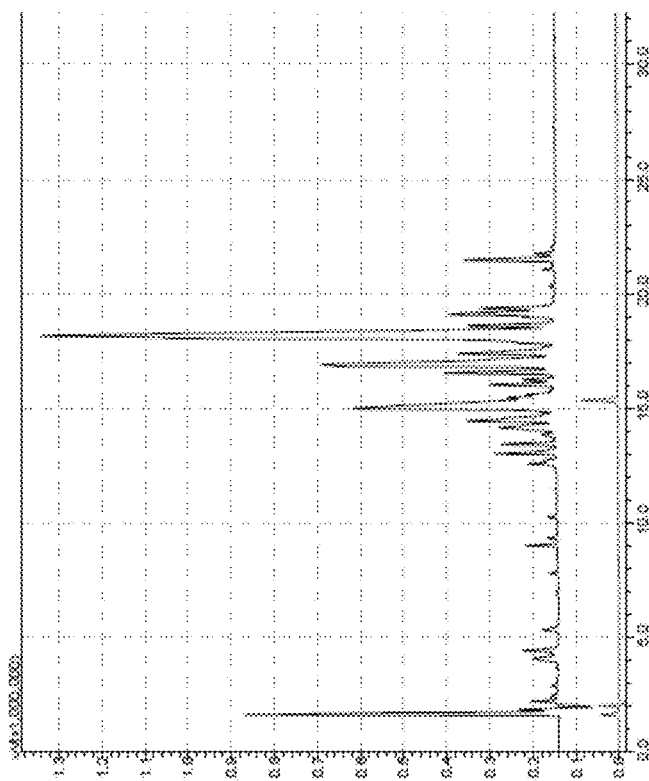
FIG. 7 shows the isolation of the Argiotoxin compound contained in the *Argiope Lobata* venom with their associated HPLC chromatogram.

FIG. 6 shows the inhibiting activity of the different sub-fractions of fraction G8. Sub-fraction 5 exhibits the lowest absorbance (between 0.3 and 0.4) and the highest inhibiting activity (between 40 and 44%). The DOPA oxidase-inhibiting activity of the fraction G8 appears to be localized in the sub-fraction 5.

Molecular Characterization by Liquid Chromatography/Mass Spectrometry

Using the LCMS-2010 EV Liquid Chromatograph mass spectrometer, and thanks to the following formula:

$$\frac{m}{z} = \frac{Mproduct + (z - 2010\ EV\ Li}{z}$$

the mass of the interest molecule has been determined.

Adducts products are: m/z+H⁺ (1 g/mol), or m/z+Na⁺ (23 g/mol), or m/z+K⁺ (39.1 g/mol).

Figure 8:
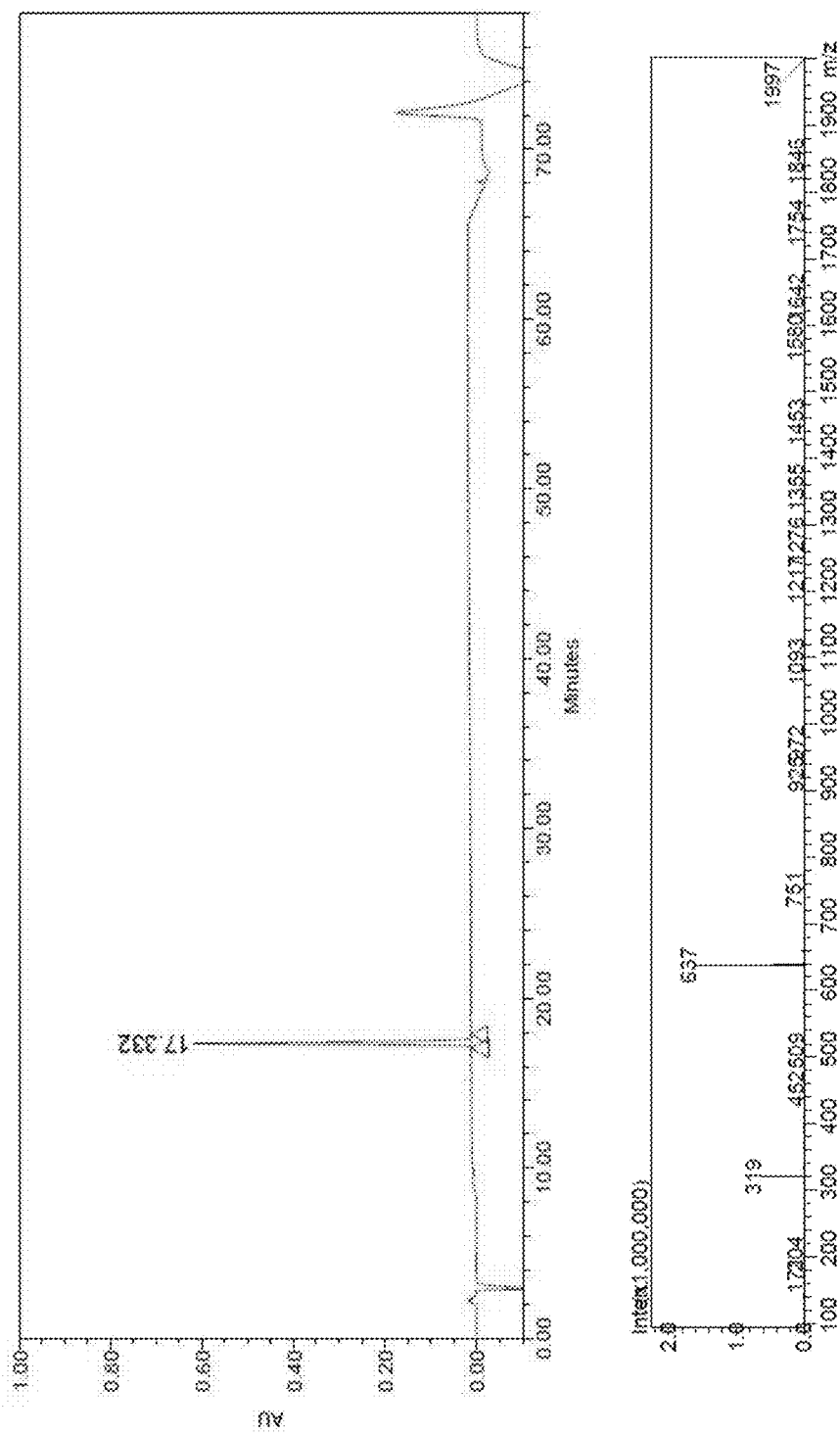
FIG. 8 shows Purified Argiotoxin chromatogram with ESI spectrum of the molecular ion [M+H+] of the identified Argiotoxin.

Here, m/z=637 has been obtained which was isolated firstly by Grishin et al., 1989, *Toxicon*. It corresponds to $M_{ARGIOTOXIN}$+H⁺. The presence of adduct product with m/z at 319, corresponds to the argiotoxin mass loaded 2 times with H+(m/z=638) and divided by 2 (638/2=319). This chromatogram which is associated to the mass spectrum, confirms that Argiotoxin-636 is the correct molecule (FIG. 8).

The Amino Acid Analysis

To confirm the Argiotoxin structure, an amino acid analysis of different batches, has been realized, thanks to IBS laboratory (Grenoble, France). All the batches were quantified by this method.

The amino acid analysis was managed as illustrated with batch 1.

The amino acid reference used is the N-Leu.

N-Leu loaded: 38904 picomol./N-Leu read: 9831 picomol.
Sample mass weight of Argiotoxin solution: 60.8 mg.
Initial volume sample: 5 mL

| A.A. | Picomol. | Res. % | A.A./Mol. | Round # |
|---|---|---|---|---|
| Asp/Asn | 3941 | 46.81 | 0.97 | 1 |
| Arg | 4216 | 50.08 | 1.03 | 1 |
| Others (Insignificant) | 262 | 3.11 | 0.06 | |

Calculation:

(3941+4216)÷2=4080 Nb pmol/*AA*

4080 m(38904 ol/*AA*)×(10004 ol/*A*)=265.55 nmol/g

The concentration of the Argiotoxin solution 1 is 171.13 μg/mL or 269.1 μM.

Thanks to the mass characterization and the amino acid analysis, the Argiotoxin structure was confirmed. This structure is comparable to the one described by GRISHIN et al. (*Toxicon*, vol. 27(5), p: 541-549, 1989). Argiotoxin is the interest molecule and will be evaluated for its potency on DOPA and DHICA oxidase activities on mushroom tyrosinase.

d) DOPA Oxidase-Inhibiting Activity of V21 i. Half Maximal Inhibitory Concentration of *Argiope Lobata* Venom

From a solution of venomat 10 mg/mL, a half maximal inhibitory concentration ($IC_{50}$) measurement has been realized.

Figure 9:
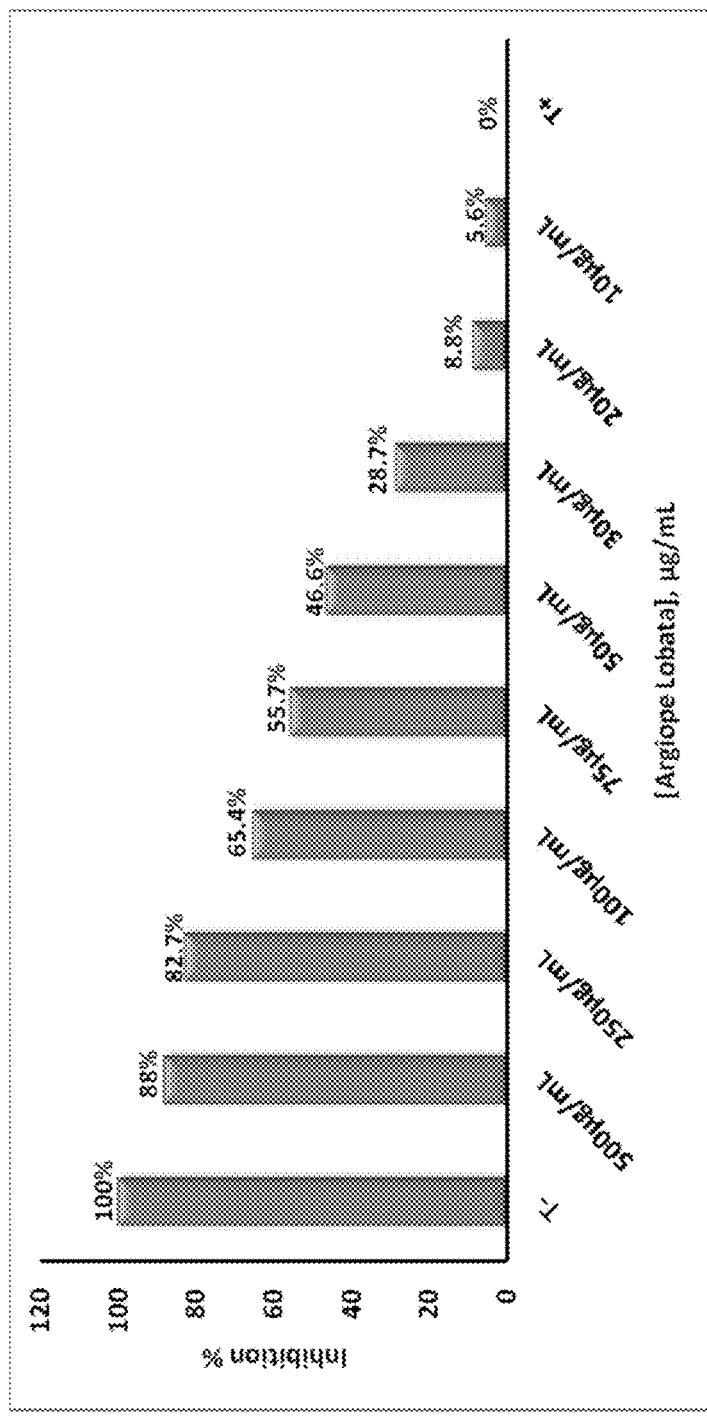
FIG. 9 shows the dose-response effect of *Argiope Lobata* venom on DOPA oxidase activity.

FIG. 9 shows the $IC_{50}$ curve of *Argiope Lobata* venom. This curve shows that 500 μg/mL of *Argiope Lobata* venom inhibits 88% of the DOPA oxidase activity and 10 μg/mL of the venom inhibits 5.6% of DOPA oxidase activity. A concentration of 62.5 μg/mL of the venom inhibits 50% of DOPA oxidase activity.

A dose-response curve with kojic acid has been realized to use as reference. It permits to correlate DOPA oxidase-inhibiting activity with another inhibitor (Data not shown).

ii. Argiotoxin Inhibitory Effect on DOPA Oxidase Activity

Argiotoxin inhibitory effect on DOPA oxidase activity was also assessed on the mushroom tyrosinase. From an argiotoxin solution at 190.8 μM, the $IC_{50}$ was determined.

Figure 10:
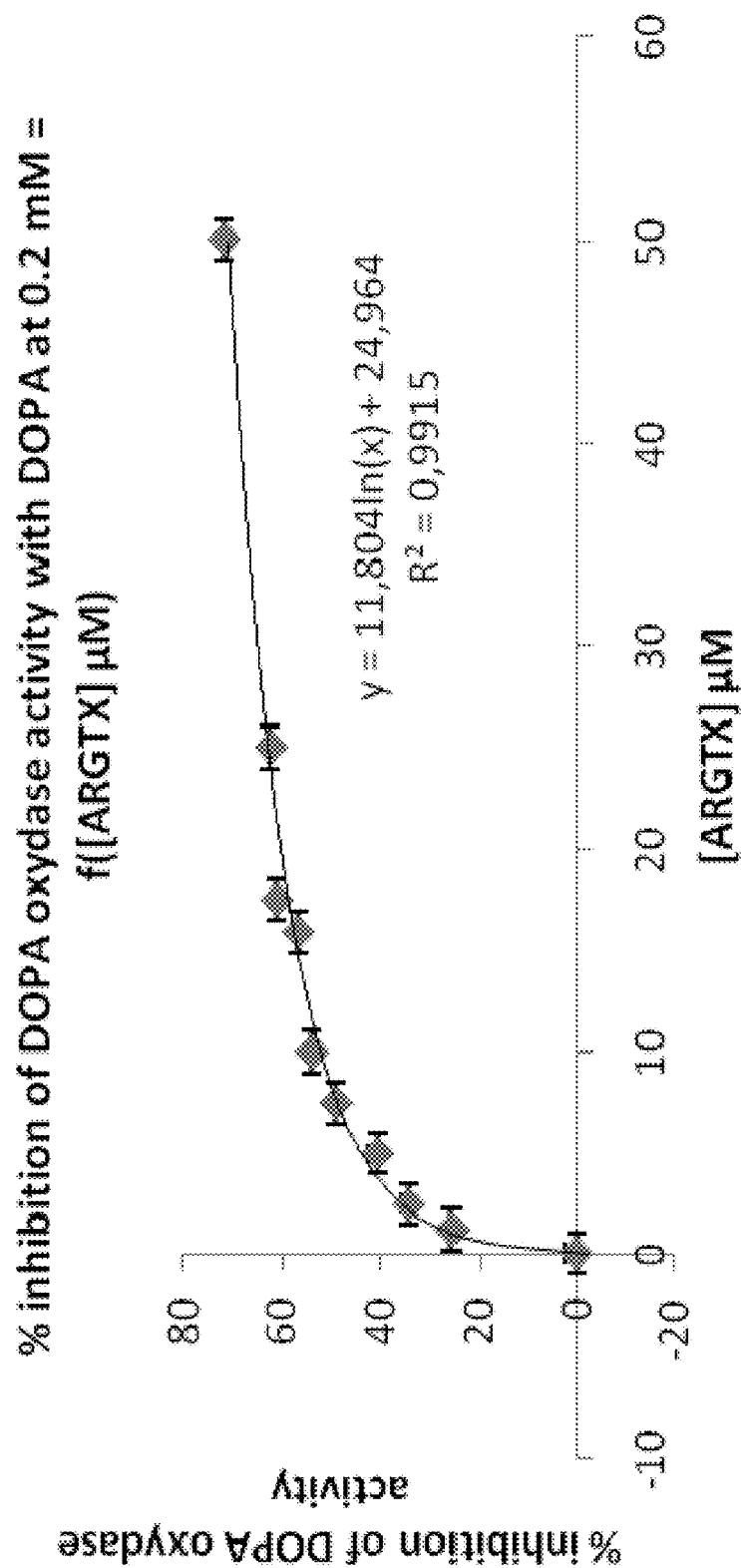
FIG. 10 shows the inhibiting activity of Argiotoxin on the DOPA oxidase activity.

FIG. 10 shows the dose-response curve of Argiotoxin on the DOPA oxidase activity. Argiotoxin display an $IC_{50}$ at 8.56 μM.

iii. Inhibitory Mechanism of Argiotoxin on DOPA Oxidase Activity

Figure 11:
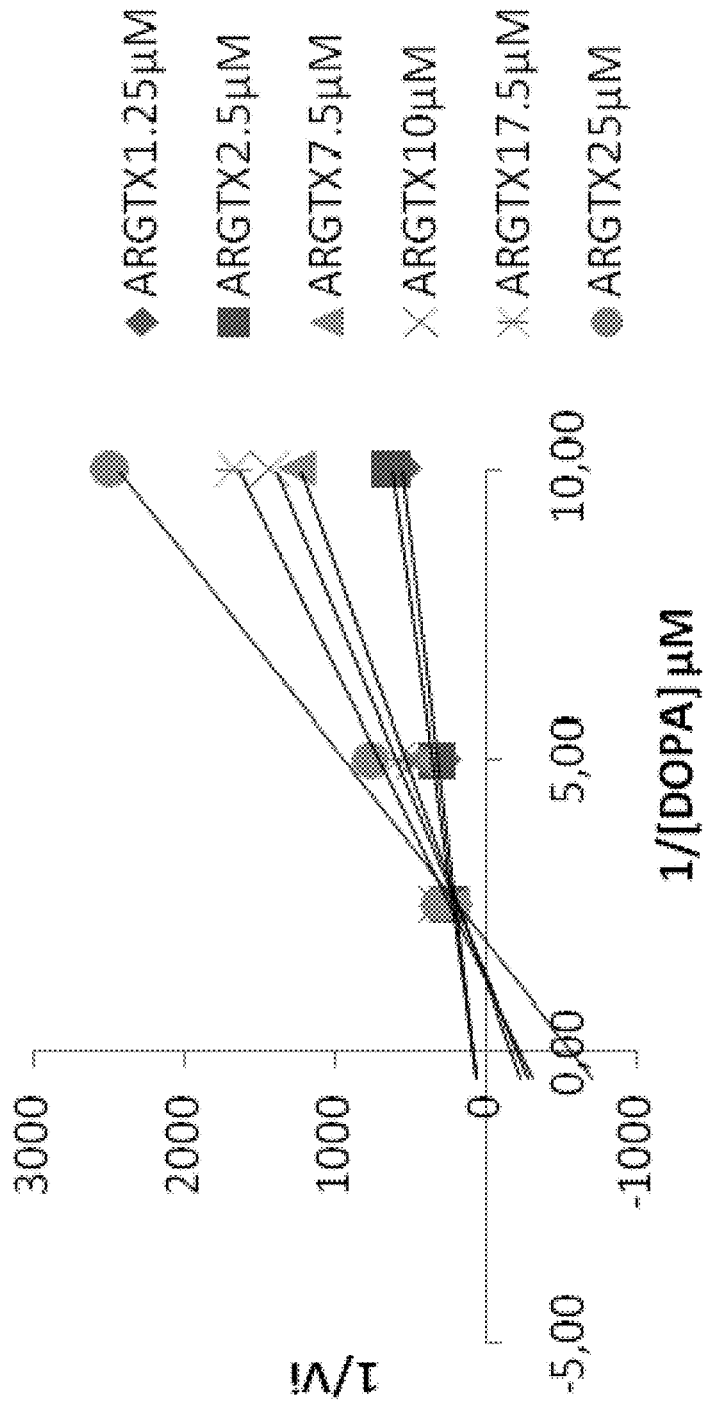
FIG. 11 shows the inhibitory mechanism of Argiotoxin on DOPA oxidase activity thanks to Lineweaver-Burk representation.

FIG. 11 represents the Lineweaver-Burk representation, a graphical interpretation allowing the determination of enzymatic parameters like the Michaelis constant (Km) characterizing the affinity between an enzyme and its substrate. The FIG. 11 shows that in the presence of increasing concentrations of Argiotoxin, the Km and the Vmax for the mushroom tyrosinase are varying, reflecting that Argiotoxin displays a mix inhibition. Thus, Argiotoxin is a non-competitive inhibitor and its binding site differs from the substrate one.

e) Calibration of 2,4-DHPAA

The 2,4-DHPAA is the aromatic portion of argiotoxine-636.

Purification of synthesized 2,4-DHPAA was done by HPLC and a calibration curve was obtained by UV spectrometry. The software which has been used is REGRESSI. Several known concentrations of DHPAA—i.e. between 0 to 1 mg/mL—were obtained and stocked.

TABLE 1

Results of the calibration assay of 2,4-DHPAA

| [DHPAA] mg/mL | Absorbances (DO) |
|---|---|
| 0.05 | 0.063 |
| 0.1 | 0.153 |
| 0.15 | 0.248 |
| 0.2 | 0.34 |
| 0.25 | 0.421 |
| 0.3 | 0.511 |
| 0.35 | 0.617 |
| 0.5 | 0.852 |
| 1 | 1.672 | f) Determination of $IC_{50}$ of 2,4-DHPAA for the DOPA Oxidase Activity

Figure 12:
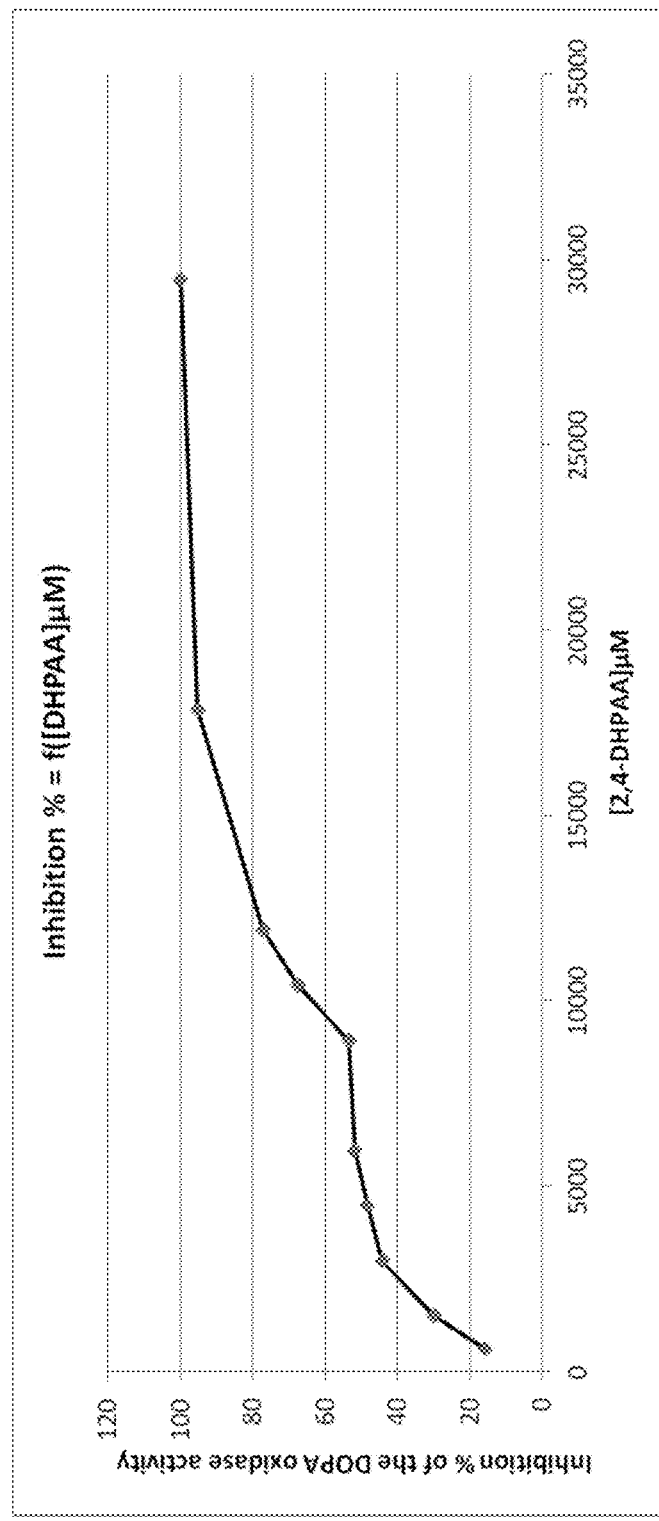
FIG. 12 shows the percentage of inhibition of the DOPA oxidase activity depending on the concentration of 2,4-DHPAA.

FIG. 12 shows the percentage of inhibition of the DOPA oxidase activity depending on the concentration of 2,4-DHPAA. This figure suggests that mushroom tyrosinase has two different active sites for the L-DOPA substrate with two different affinities. So, the 2,4-DHPAA would be a competitive inhibitor. Here, the activity is lower than for the whole Argiotoxin compound and around 6 mM. This result reflects that the entire activity of the argiotoxin compound seems to be not only restricted to the head part of the compound.

g) Argiotoxin Effect on DHICA Oxidase Activity

The mushroom tyrosinase has both the DOPA and the DHICA oxidase activities (SUGUMARAN et al, *Pigment Cell Res.*, vol. 12(2), p: 118-25, 1999). The DHICA oxidase activity is specifically required for the biosynthesis of black/brown pigment. The ability of Argiotoxin to inhibits this activity is evaluated thank to the mushroom tyrosinase.

Figure 14:
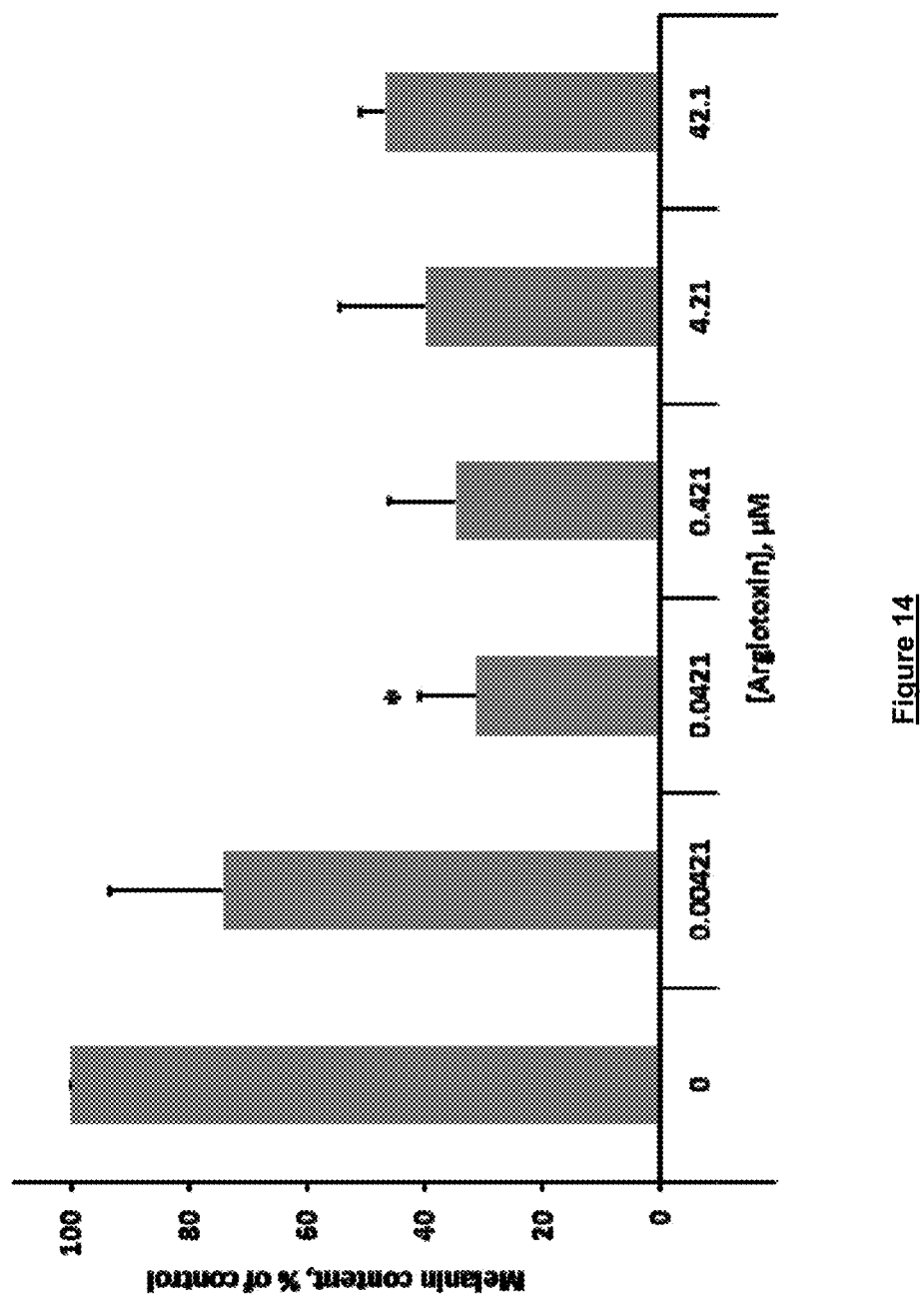
FIG. 14 shows the Argiotoxin inhibiting activity on melanogenesis in a cell-based assay.

A dose-dependent inhibition is visible up to 100 μM of Argiotoxin (FIG. 14). The experimental conditions are the same as previously mentioned. DHICA was used as substrate at 0.25 mM.

Figure 13:
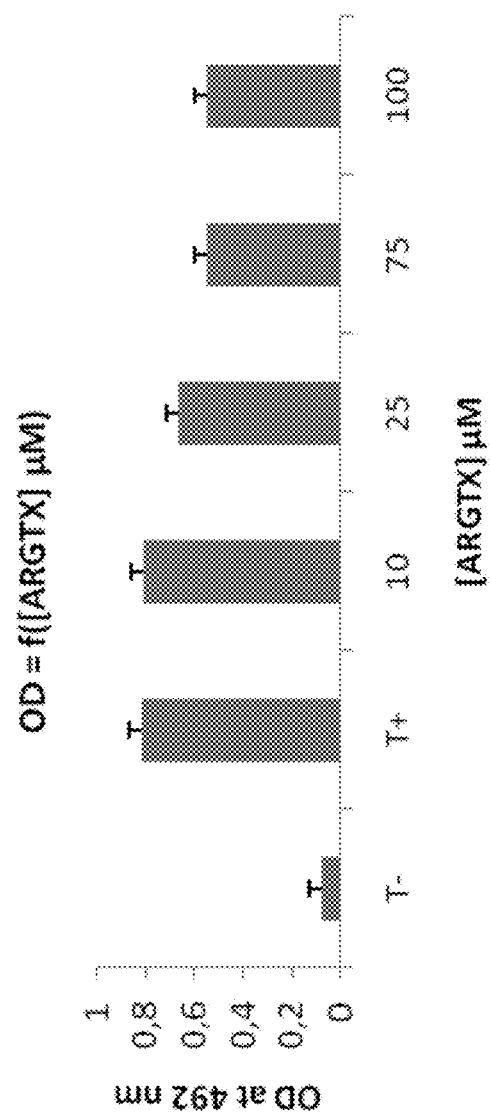
FIG. 13 shows the absorbance and thus inhibiting activity of Argiotoxin on DHICA oxidase activity.
Figure 13:
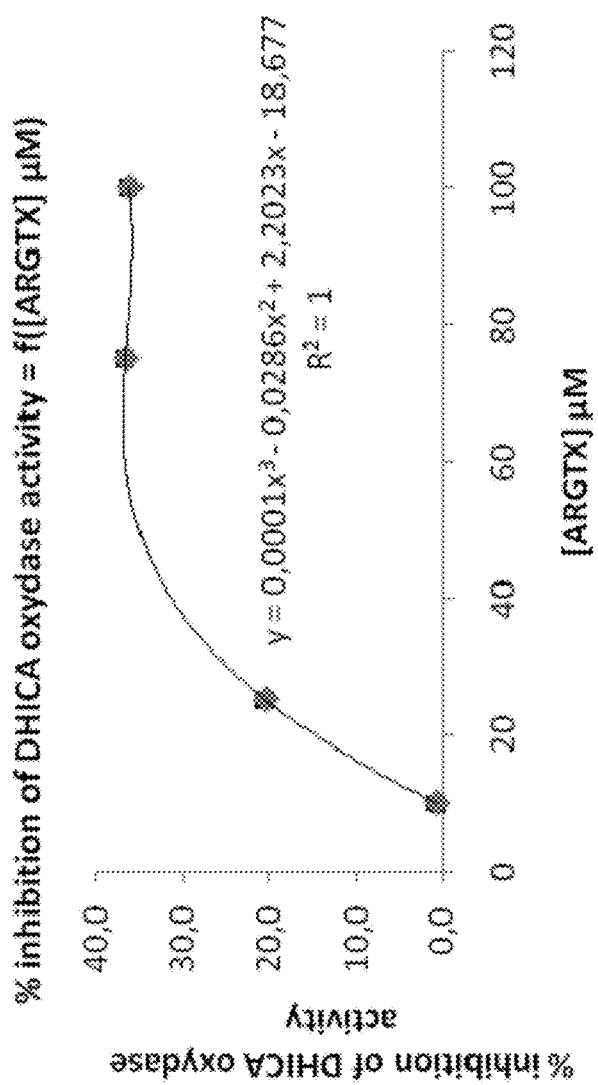

FIG. 13 shows that Argiotoxin inhibits the DHICA oxidase activity of mushroom tyrosinase in a dose-dependent manner up to 75 μM.

2) In Vivo Experiments

Before going further in the evaluation of the potential use of argiotoxin as a skin bleaching agent, its cytotoxic potency is evaluated at the maximal concentration (42.1 μM) displaying an effect in vivo. Argiotoxin presents neither cell death nor cytotoxicity at 42.1 μM respectively evaluated by the MTT or the LDH cell-based assays (Data not shown).

a) Melanogenesis Assay

B16F10 are murine melanoma cells, a cell line able to produce melanin and considered as an accurate model to assess melanogenesis inhibition. Cells were seeded at $5.10^4$ cells/well in a P24 well plate and stimulated by 100 nM of α-MSH, the melanin-stimulating hormone. 24 h later, cells were treated by increasing concentration of kojic acid as a control (from 0 to 250 μM) and from 0 to 42.1 μM for argiotoxin. 48 h later, according to SIEGRIST & EBERLE (*Analytical Biochemistry*, vol. 159(1), p: 191-7, 1986), the amount of melanin released in the medium was spectrophotometrically measured at 405 nm and normalised to the protein content.

The argiotoxin is also able to block the melanogenesis in B16F10 in a dose-dependent manner and present an $IC_{50}$ around 0.01 μM (FIG. 14).

The head part of the argiotoxin which is identified as the DHPA was also tested on this cellular assay to evaluate whether the ex-vivo activity of Argiotoxin relies on the activity of this known compound. The protocol was the same as previously described for the argiotoxin. As a control, kojic acid was used in the same range of concentration.

Figure 15:
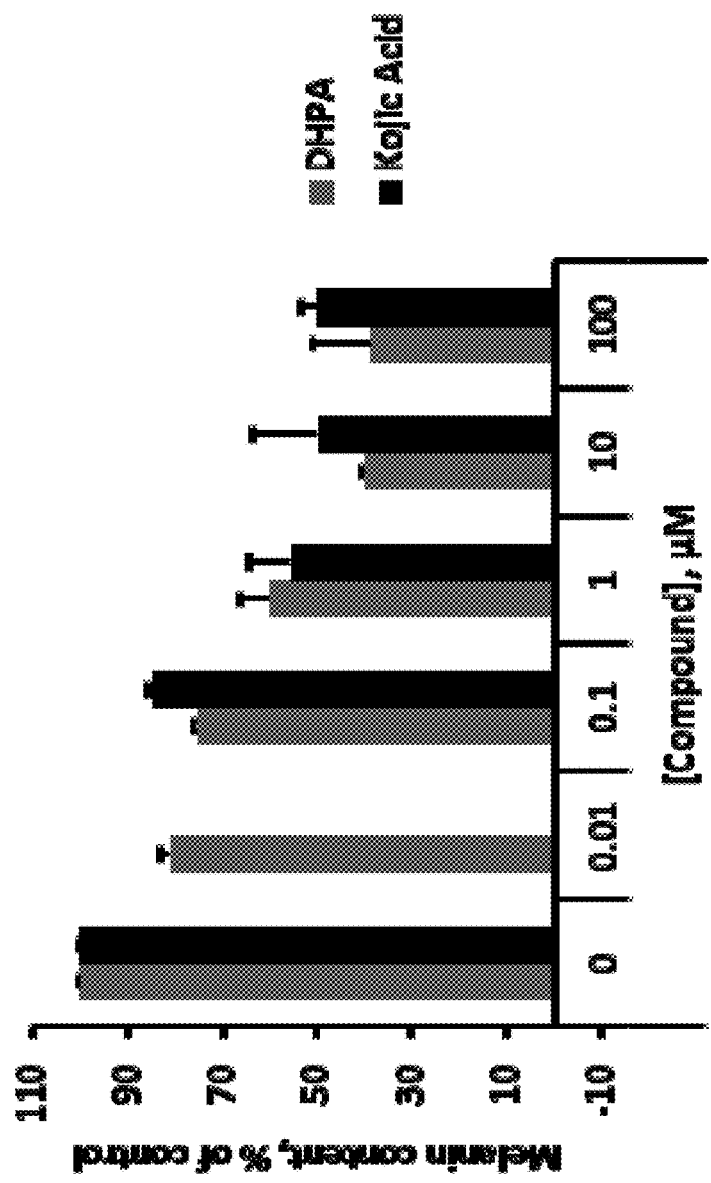
FIG. 15 compares the potency of 2,4-DHPA compound and Kojic Acid on the melanogenic cell-based assay.

Both compounds show a dose-response profile (FIG. 15). DHPA presents an $IC_{50}$ comparable to the kojic acid and around 5 μM. The presence of the DHPA group in the argiotoxin could only partially explain the high potency of the argiotoxin. Indeed, argiotoxin presents a 100 fold higher activity on this cellular assay suggesting that the activity of the argiotoxin is not concentrate in the head part of the molecule.

b) Western Blot Analysis

To explore the mechanism of action of Argiotoxin in melanogenesis processes, we assess its ability to regulate the protein expression of two enzymes, the tyrosinase and TRP1 which is implicated in the biosynthesis of black/brown pigments specifically. Western blot analyses were performed on B16F10 cells treated as previously described.

Figure 16:
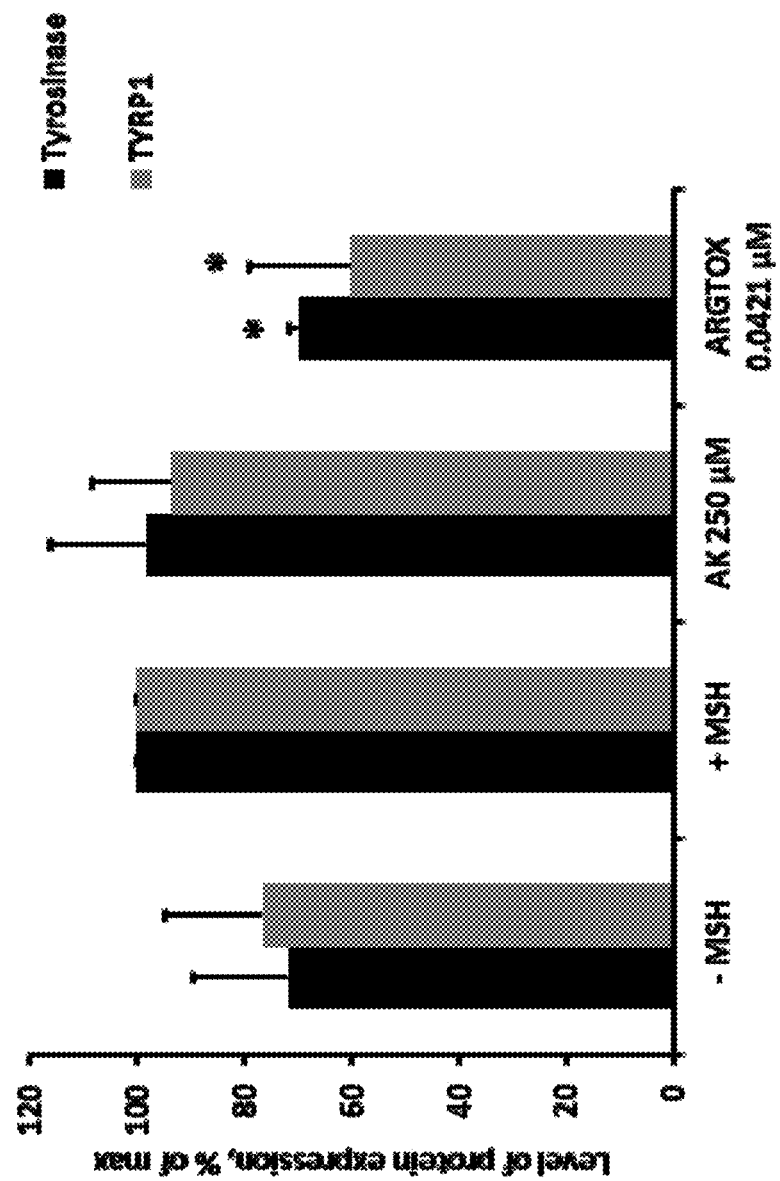
FIG. 16 shows the regulatory effect of Argiotoxin compared to Kojic acid on both Tyrosinase and TRP1 expression.

FIG. 16 shows that as expected αMSH stimulation enhances the expression of tyrosinase and TRP1. Kojic acid treatment faintly decreases the expression of murine tyrosinase or TRP1 protein. Contrary to the reference inhibitor, Argiotoxin display a significant inhibition of the expression of both proteins. Argiotoxin reduces significantly the expression of tyrosinase and TRP1 proteins suggesting that the compound may directly interact with these enzymes to degrade them or interfere with their biosynthesis pathway.

The inhibition of TRP1 expression by Argiotoxin highlights the fact that this compound may have a different mechanism of action compared to classic inhibitors like kojic acid and confirms its relevance in cosmetic to develop specific skin-bleaching products targeting phototypes V and VI.

III. Synthetic Analogs Whitening Activity

1) Synthetic Analogs

The argiotoxin synthetic analogs are listed in table I in reference to formula (1).

TABLE I

| N° | R1 | R2 | R3 | R4 | R5 | R6 |
|---|---|---|---|---|---|---|
| 1 | Tyr | Asparagine (Asn) | n' = 7 | absent | absent | Arginine (Arg) |
| 2 | $(OH)_2C_6H_3$—$CH_2$—$C(=O)$- | Asn | n' = 5 | n = 6 | absent | Arg |
| 3 | H | Asn | n' = 7 | absent | absent | Arg |
| 4 | H | Asn | n' = 6 | absent | absent | Arg |
| 5 | H | Asn | n' = 5 | absent | absent | Arg |
| 6 | H | Asn | n' = 7 | n'' = 7 | absent | Arg |
| 8 | H | Asn | n' = 7 | n'' = 6 | absent | Arg |
| 9 | H | Asn | n' = 7 | n'' = 5 | absent | Arg |
| 10 | H | Asn | n' = 6 | n'' = 6 | absent | Arg |
| 12 | H | Asn | n' = 6 | n'' = 5 | absent | Arg |
| 13 | H | Asn | n' = 6 | n'' = 4 | absent | Arg |
| 14 | H | Asn | n' = 6 | n'' = 7 | absent | Arg |
| 15 | H | Asn | n' = 5 | n'' = 6 | absent | Arg |
| 16 | H | Asn | n' = 5 | n'' = 5 | absent | Arg |
| 17 | H | Asn | n' = 7 | n'' = 3 | n''' = 3 | Arg |
| 18 | H | Asn | n' = 6 | n'' = 4 | n''' = 3 | Arg |
| 19 | H | Asn | n' = 6 | n'' = 3 | n''' = 4 | Arg |
| 20 | H | Asn | n' = 6 | n'' = 3 | n''' = 3 | Arg |
| 21 | H | Asn | n' = 5 | n'' = 4 | n''' = 3 | Arg |
| 22 | H | Asn | n' = 5 | n'' = 3 | n''' = 4 | Arg |
| 23 | H | Asn | n' = 5 | n'' = 3 | n''' = 3 | Arg |
| 24 | H | Asn | n' = 4 | n'' = 3 | n''' = 3 | Arg |
| 25 | H | Asn | n' = 4 | n'' = 3 | n''' = 5 | Arg |
| 26 | H | Asn | n' = 4 | n'' = 3 | n''' = 3 | Arg |
| 27 | H | Asn | n' = 3 | n'' = 4 | n''' = 4 | Arg |
| 28 | H | Asn | n' = 3 | n'' = 5 | n''' = 3 | Arg |

TABLE I-continued

| N° | R1 | R2  | R3      | R4      | R5       | R6  |
|----|----|-----|---------|---------|----------|-----|
| 29 | H  | Asn | n' = 2  | n" = 5  | n''' = 4 | Arg |
| 30 | H  | Asn | n' = 2  | n" = 6  | n''' = 3 | Arg |

2) Inhibition of DOPA and DHICA Oxidase Activities

The abovementioned analogs synthetics are tested at different concentration on the mushroom tyrosinase as disclosed previously. Argiotoxin is used as positive control.

3) In Vivo Experiment

The analogs synthetics having an $IC_{50}$ inferior to 10 µM for DOPA and/or DHICA activities are tested on melanogenesis as described previously. Again, Argiotoxin is used as a positive control.

The invention claimed is:

1. A method for whitening and depigmenting black human skin in need thereof comprising topically applying with sponges, swabs, pads or wipes said black human skin, a whitening and depigmenting amount of a spider venom of *Argiope Lobata* or an isolated spider venom molecule represented by formula (2):

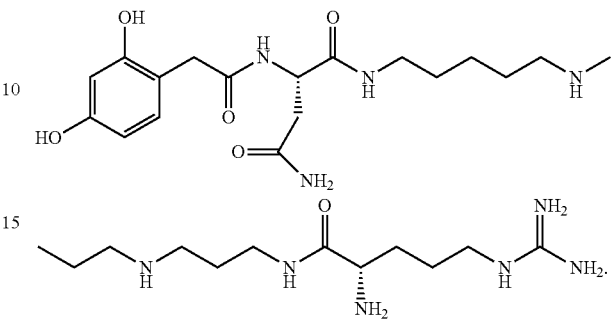

(2)